US008090541B2

(12) United States Patent
Castonguay et al.

(10) Patent No.: US 8,090,541 B2
(45) Date of Patent: Jan. 3, 2012

(54) MAP-BASED GENOME MINING METHOD FOR IDENTIFYING REGULATORY LOCI CONTROLLING THE LEVEL OF GENE TRANSCRIPTS AND PRODUCTS

(75) Inventors: Yves Castonguay, Sainte-Foy (CA); Louise S. O'Donoughue, Mont St.-Hilaire, CA (US); Serge Laberge, Sillery (CA); Antonio F. Monroy, Montreal (CA); Louis P. Vezina, Neuville (CA); Benoit S. Landry, L'Acadie (CA)

(73) Assignees: DNA Landmarks Inc., Quebec (CA); Her Majesty the Queen in the Right of Canada as Represented by the Minister of Agriculture and Agri-Food Soils and Crops Research and Dev, Quebec (CA)

( * ) Notice: Subject to any disclaimer, the term of this patent is extended or adjusted under 35 U.S.C. 154(b) by 901 days.

(21) Appl. No.: 11/923,946

(22) Filed: Oct. 25, 2007

(65) Prior Publication Data
US 2008/0233574 A1 Sep. 25, 2008

Related U.S. Application Data

(63) Continuation of application No. 10/333,150, filed as application No. PCT/CA01/01028 on Jul. 17, 2001, now abandoned.

(60) Provisional application No. 60/218,765, filed on Jul. 17, 2000.

(51) Int. Cl.
*G01N 33/48* (2006.01)
(52) U.S. Cl. ...................................... 702/19
(58) Field of Classification Search .................. 702/19
See application file for complete search history.

(56) References Cited

U.S. PATENT DOCUMENTS

| 5,948,953 A | 9/1999 | Webb |
| 6,368,806 B1 | 4/2002 | Openshaw et al. |
| 2004/0091933 A1 | 5/2004 | Stoughton et al. |

FOREIGN PATENT DOCUMENTS

| WO | WO99/31964 | 7/1999 |
| WO | WO99/13107 | 9/1999 |
| WO | WO99/67367 | 12/1999 |
| WO | WO00/18963 | 4/2000 |

OTHER PUBLICATIONS

Foolad et al. "RFLP Mapping of QTLs Conferring Salt Tolerance During Germination in an Interspecific Cross of Tomato," Theor. Appl. Geneti. (1998) vol. 97, pp. 1133-1144.*
Choi et al. "The Barley (*Hordeum vulgare* L.) Dehydrin Multigene Family: Sequenes, Allele Types, Chromosome Assignments, and Expression Characteristics of 11 Dhn Genes of cv Dicktoo," Theroretical Applied Genetics (1999) vol. 98, pp. 1234-1247.*
Alpert, et al., High-Resolution Mapping and Isolation of a Yeast Artificial Chromosome Contig Containing fw2.2: A Major Fruit Weight Quantitative Trait Locus in Tomato, Proc. Natl. Acad. Sci. USA, 1996, 93:15503-15507.
Choi, et al., The Barley (*Hordeum vulgare* L.) Dehydrin Multigene Family: Sequences, Allele Types, Chromosome Assignments, and Expression Characteristics of 11 Dhn Genes of cv Dicktoo, Theor. Appl. Genet., 1999, 98:1234-1247.
Cushman, et al., Genomic Approaches to Plant Stress Tolerance, Current Opinion in Plant Biology, 2000, 3:117-124.
Foolad, et al., RFLP Mapping of QTLs Conferring Salt Tolerance During Germination in an Interspecific Cross of Tomato, Theor. Appl. Genet., 1998, 97:1133-1144.
United States Patent and Trademark Office, Office Action Summary and Detailed Action, U.S. Appl. No. 10/333,150, Nov. 21, 2005.
Response to United States Patent and Trademark Office Nov. 21, 2005 Restriction Requirement, U.S. Appl. No. 10/333,150, Dec. 21, 2005.
United States Patent and Trademark Office, Office Action Summary and Detailed Action, U.S. Appl. No. 10/333,150, Feb. 16, 2006.
Response to United States Patent and Trademark Office Feb. 16, 2006 Office Action, U.S. Appl. No. 10/333,150, May 16, 2006.
United States Patent and Trademark Office, Office Action Summary and Detailed Action, U.S. Appl. No. 10/333,150, Aug. 9, 2006.
Response to United States Patent and Trademark Office Aug. 9, 2006 Final Office Action, U.S. Appl. No. 10/333,150, Oct. 9, 2006.
United States Patent and Trademark Office, Office Action Summary and Detailed Action, U.S. Appl. No. 10/333,150, Nov. 9, 2006.
Response to United States Patent and Trademark Office Nov. 9, 2006 Office Action, U.S. Appl. No. 10/333,150, Feb. 9, 2007.
United States Patent and Trademark Office, Office Action Summary and Detailed Action, U.S. Appl. No. 10/333,150, Apr. 27, 2007.
United States Patent and Trademark Office, Notice of Abandonment, U.S. Appl. No. 10/333,150, Dec. 13, 2007.
International Search Report, PCT/CA01/01028, Jan. 15, 2003.
*Canadian Journal of Plant Science* 56:203-205 (1976) "Notes, Anik Alfalfa".
*Canadian Journal of Plant Science* 63:547-549 (1983) "Note, Apica Alfalfa".

(Continued)

*Primary Examiner* — Jerry Lin
(74) *Attorney, Agent, or Firm* — Quarles & Brady LLP; Sara D. Vinarov

(57) ABSTRACT

A method is provided for identifying one or more regions within a genome of an organism of interest that mediate the expression of one or more genes of interest. The method comprises identifying a first organism of interest exhibiting a measurable response to an environmental stimulus; identifying a second organism of interest that lacks or does not exhibit as strong a response to the stimulus as compared with the first organism of interest; crossing the first and second organisms of interest to produce a population of progeny; extracting RNA from each individual population of progeny; quantifying a level of gene expression for one or more genes of interest that are associated with the response to an environmental stimulus; identifying one or more Quantitative Trait Locus (QTL), wherein gene expression level is a quantitative trait, and using one or more markers comprising one or more regulatory sequences to mediate said expression of said one or more genes of interest induced by said environmental stimulus; and identifying the one or more regulatory sequences located at said one or more QTL.

12 Claims, 13 Drawing Sheets

OTHER PUBLICATIONS

Bingham, E. T., et al., "Cultivated Alfalfa at the Diploid Level: Origin, Reproductive Stability, and Yield of Seed and Forage," *Crop Science* 19:97-100 (1979).

Bryne, P. F., et al., "Quantitative trait loci and metabolic pathways: Genetic control of the concentration of maysin, a corn earworm resistance factor, in maize silks," *Proc. Natl. Acad. Sci. USA* 93:8820-8825 (1996).

Castonguay, Y., et al., "Freezing Tolerance and Alteration of Translatable mRNAs in Alfalfa (*Medicago sativa* L.) Hardened at Subzero Temperatures," *Plant Cell Physiol.* 34:31-38 (1993).

Castonguay Y., et al., "A cold-induced gene from *Medicago sativa* encodes a bimodular protein similar to developmentally regulated proteins," *Plant Molecular Biology* 24:799-804 (1994).

Castonguay, Y., et al., "Temperature and Drought Stress," *CAB International, Biotechnology and the Improvement of Forage Legumes* 175-202 (1997).

Cicila G., et al., "Identifying Candidate Genes for Blood Pressure Quantitative Trail Loci Using Differential Gene Expression and a Panel of Congenic Strains", *Hypertens Res.* 21:289-296 (1998).

Damerval, C., et al., "Quantitative Trail Loci Underlying Gene Product Variation: A Novel Perspective for Analyzing Regulation of Genome Expression," *Genetics* 137:289-301 (1994).

Daniels, J., et al., "Molecular Genetic Studies of Cognitive Ability," *Human Biology* 70:281-296 (1998).

Desgagnes, R., et al, "Genetic transformation of commercial breeding lines of alfalfa (*Medicago sativa*)," *Plant Cell. Tissue and Organ Culture* 42:129-140 (1995).

Doyle, J., et al., "Isolation of Plant DNA From Fresh Tissue," *Focus* 12 No. 1 13-15 (1990).

Dumas, P., et al., "Mapping of quantitative trail loci (QTL) of differential stress gen expression in rat recombinant inbred strains," *Journal of Hypertension* 18:545-551 (2000).

Fourney, R. M., et al., "Northern Blotting: Efficient RNA Staining and Transfer," *Focus* 10 5-7 (1988).

Hirt, H., "Transcriptional upregulation of signaling pathways: more complex than anticipated?," *Elsevier Science* 4:7-8 (1999).

Jaglo-Ottesen, K. R., et al, "*Arabidopsis CBF*-1 Overexpression Induces *COR* Genes and Enhances Freezing Tolerance," *Science* 280:104-106 (1998).

Kim, J. C., et al., "A novel cold-inducible zinc finger protein front soybean, SCOF-1, enhances cold tolerance in transgenic plants," *The Plant Journal* 25:247-259 (2001).

LaBerge S., et al., "New Cold- and Drought-Regulated Gene from *Medicago sativa*," *Plant Physiol.* 101:1411-1412 (1993).

Lander, E. S., et al., "MAPMAKER: An Interactive Computer Package for Constructing Primary Genetic Linkage Maps of Experimental and Natural Populations," *Genomics* 1:174-181 (1987).

Lander, E. S., et al, "Mapping Mendelian Factors Underlying Quantitative Traits Using RFLP Linkage Maps," *Genetics* 121:185-199 (1989).

Machleder, D., et al., "Complex Genetic Control of HDL Levels in Mice in Response to an Atherogenic Diet," *J. Clin. Invest.* 99:1406-1419 (1997).

Martin, G. B., et al., "Map-Based Cloning of a Protein Kinase Gene Conferring Disease Resistance in Tomato," *Science* 252:1432-1436 (1991).

Monroy, A. F., et al., "A New Cold-Induced Alfalfa Gene is Associated with Enhanced Hardening at Subzero Temperature," *Plant Physiol.* 102:873-879 (1993).

Munnik, T., et al., "Osmotic stress activates distinct lipid and MAPK signalling pathways in plants," *FEBS Letters* 498:172-178 (2001).

Paterson, A. H., et al., "Resolution of quantitative traits into Mendelian factors by using a complete linkage map of restriction fragment length polymorphisms," *Nature* 335:721-726 (1988).

Pelleschi, S., et al, "*Ivr2*, a candidate gene for a QTL of vacuolar invertase activity in maize leaves. Gene-specific expression under water stress," *Plant Molecular Biology* 39:373-380 (1999).

Prioul, J., et al., "Dissecting complex physiological functions through the use of molecular quantitative genetics," *Journal of Experimental Botany* 48:1151-1163 (1997).

Proul, J., et al., "From QTLs for enzyme activity to candidate genes in maize," *Journal of Experimental Botany* 50:1281-1288 (1999).

Tsaftaris, S. A., "Molecular aspects of heterosis in plants," *Physiologia Plantarum* 94:362-370 (1995).

van Zee, K., et al, "Cold-Specific Induction of a Dehydrin Gene Family Member in Barley," *Plant Physiol.* 108:1233-1239 (1995).

Vos, P., et al., "AFLP: a new technique for DNA fingerprinting," *Nucleic Acids Research* 23:4407-4414 (1995).

Cicila, G.T., et al., "Identifying Candidate Genes for Blood Pressure Quantitative Trait Loci Using Differential Gene Expression and a Panel of Congenic Strains," Hypertens Res 21:289-296 (1998).

Dumas, P., et al., "Mapping of quantitative trait loci (QTL) of differential stress gene expression in rat recombinant inbred strains," J. Hypertension 18:545-551 (2000).

Machleder, D., et al., "Complex Genetic Control of HDL Levels in Mice in Response to an Atherogenic Diet," J. Clin, Invest. 99:1046-1419 (1997).

Pelleschi, S., et al., "Ivr2, a candidate gene for a QTL of vacuolar invertase activity in maize leaves. Gene-specific expression under water stress." Plant Molecular Biology 39:373-380 (1999).

Tsaftaris, S.A., "Molecular aspects of heterosis in plants," Physiologia Plantarum 94:362-370 (1995).

van Zee, K., et al., "Cold-Specific Induction of a Dehydrin Gene Family Member in Barley," Plant Physiol. 108:1233-1239 (1995).

\* cited by examiner

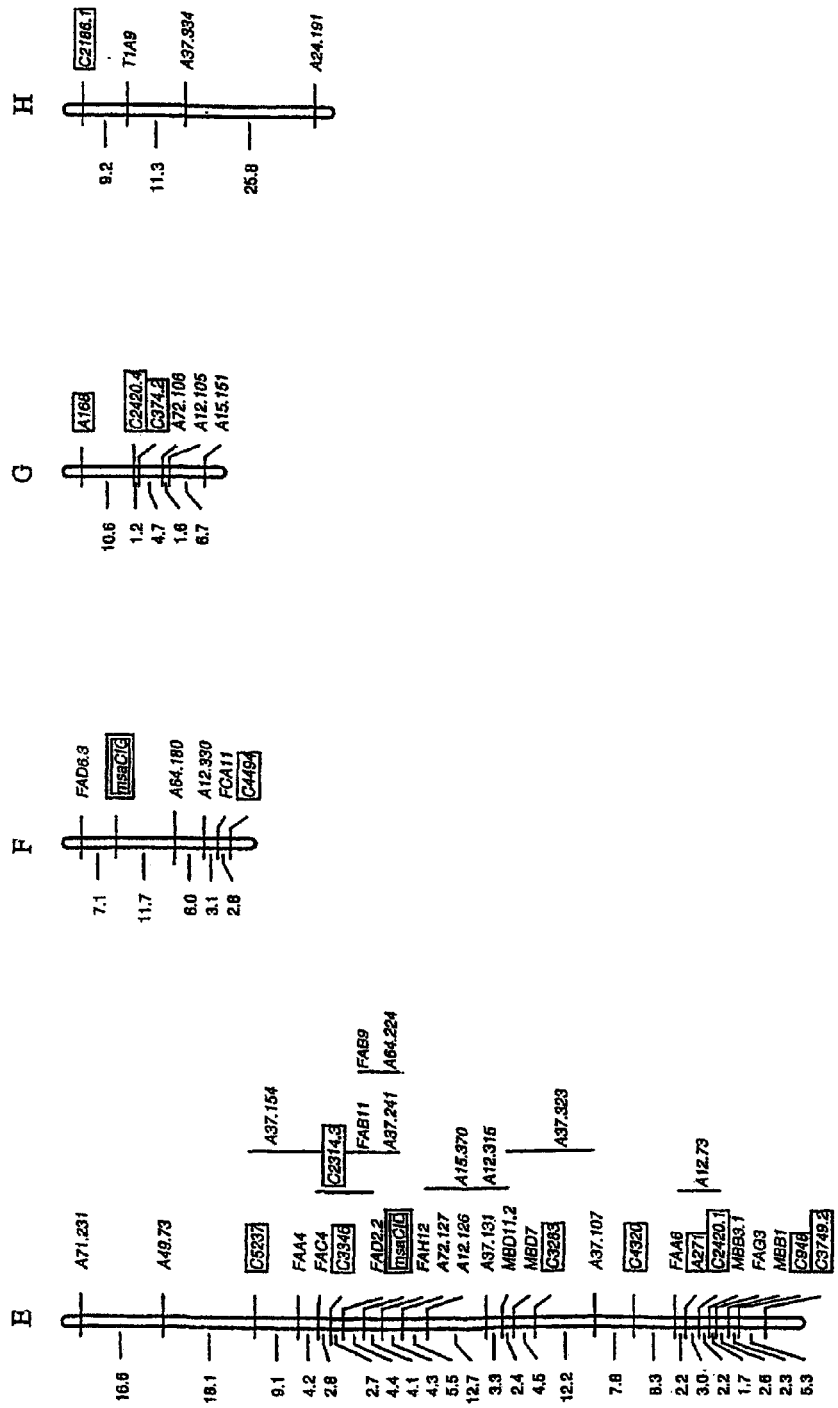
Figure 1 con't

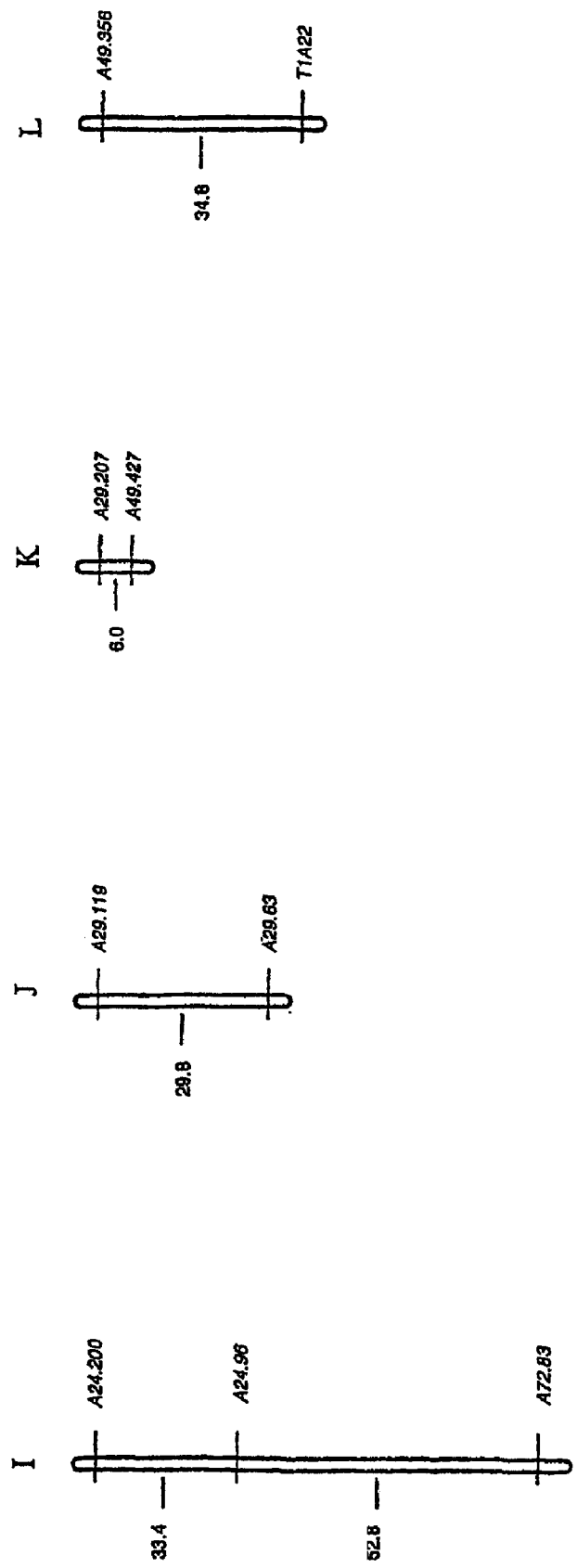
Figure 1 con't

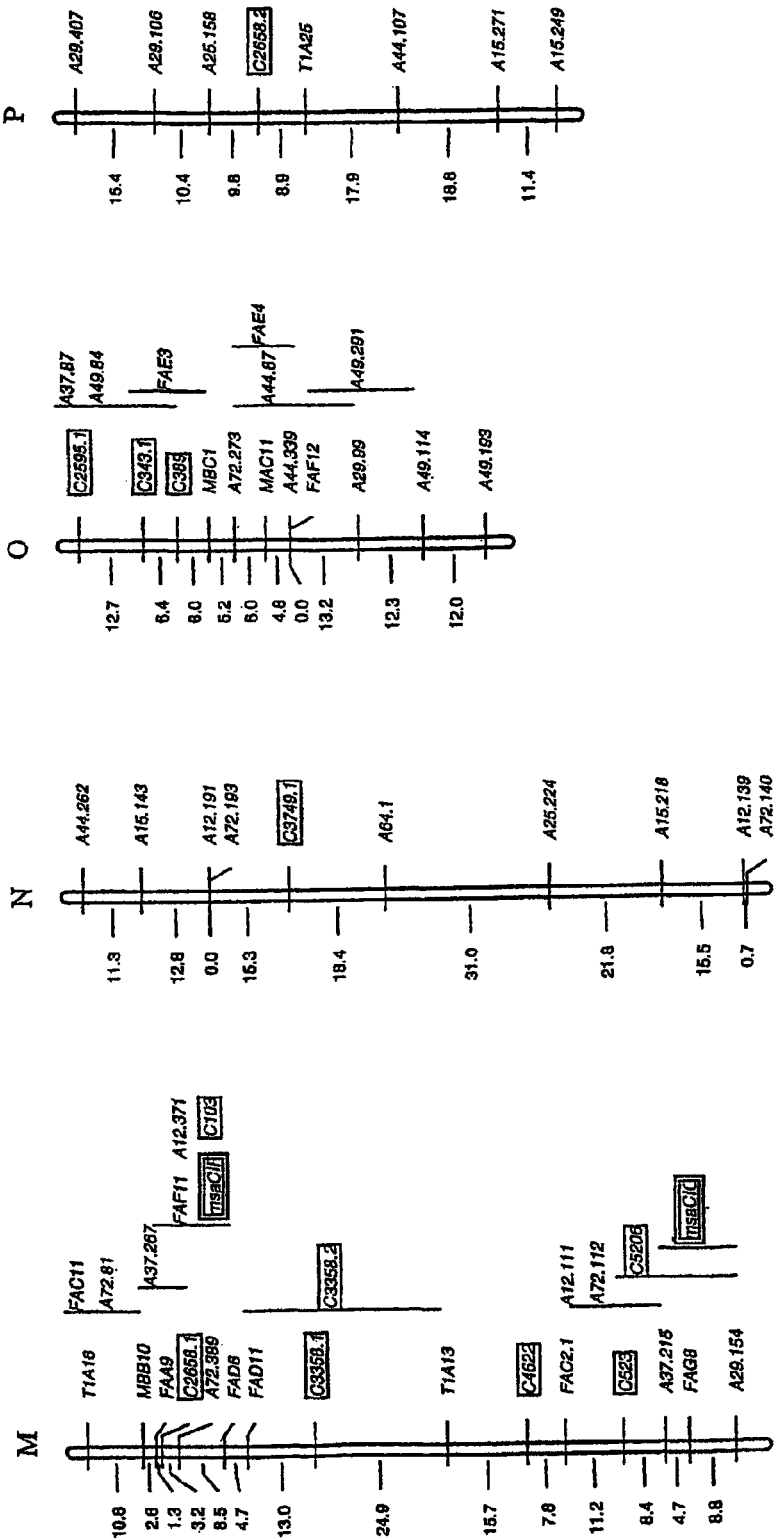
Figure 1 con't

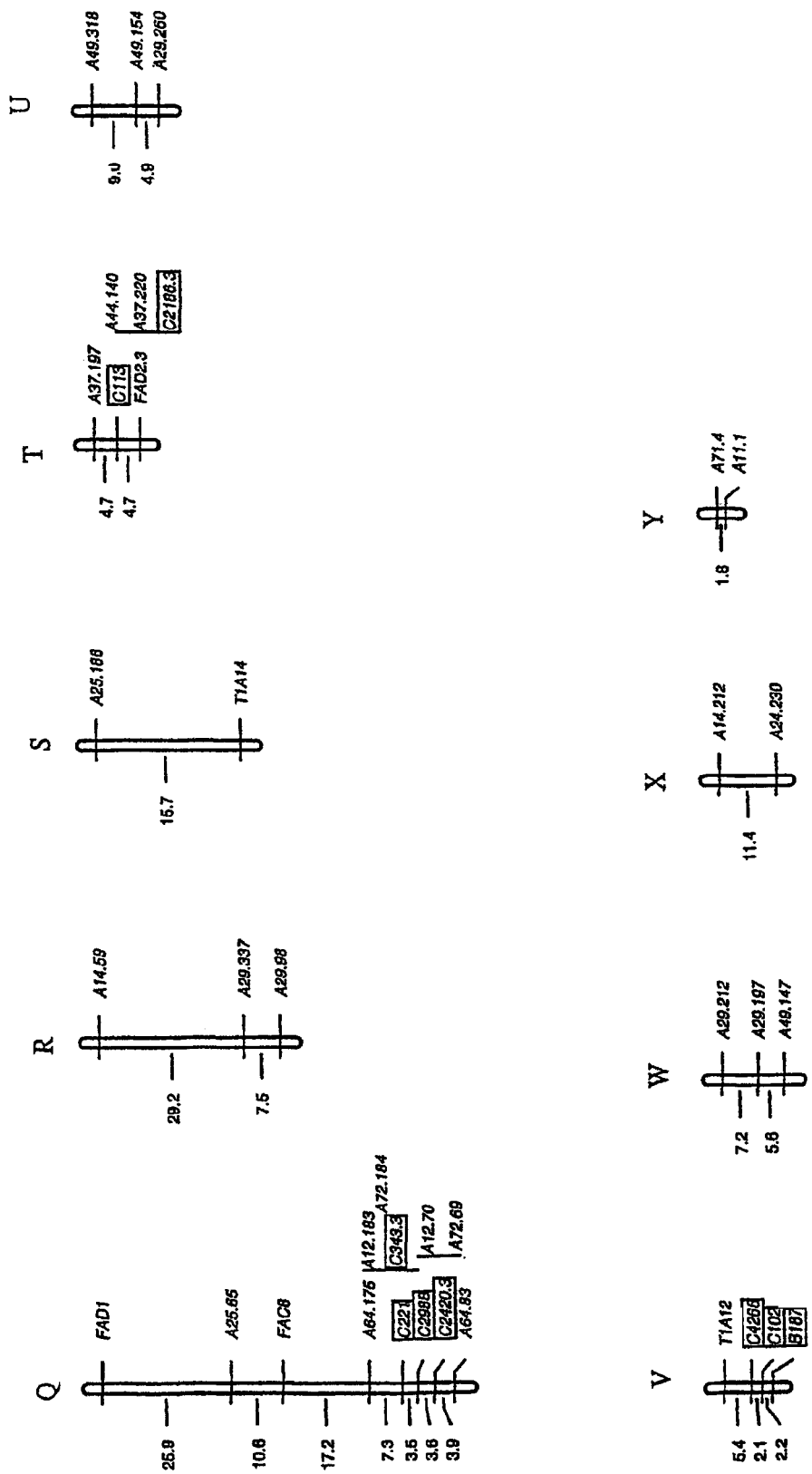
Figure 1 con't

Linkage group A

Crown

Leaf

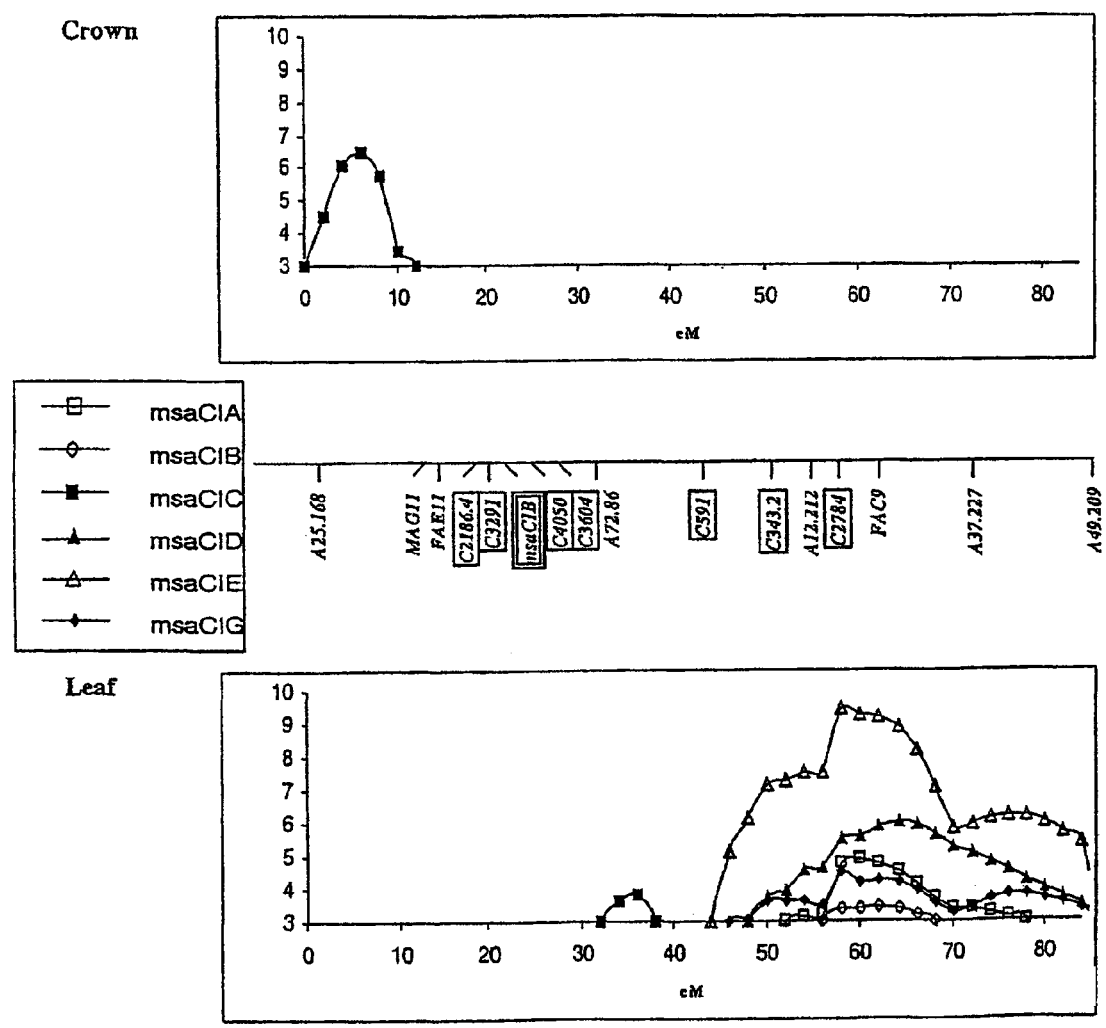
Figure 2 con't

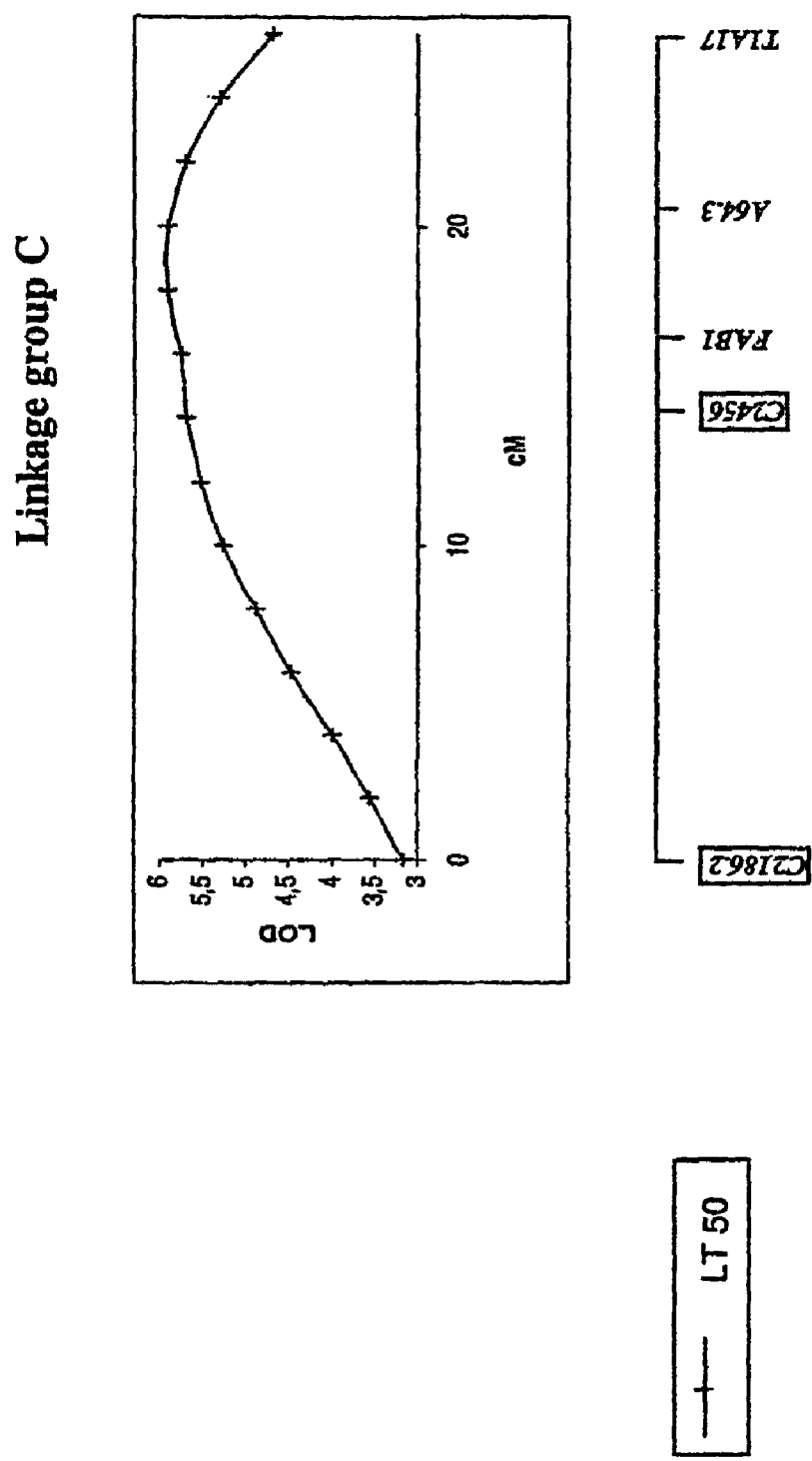
Figure 2 con't

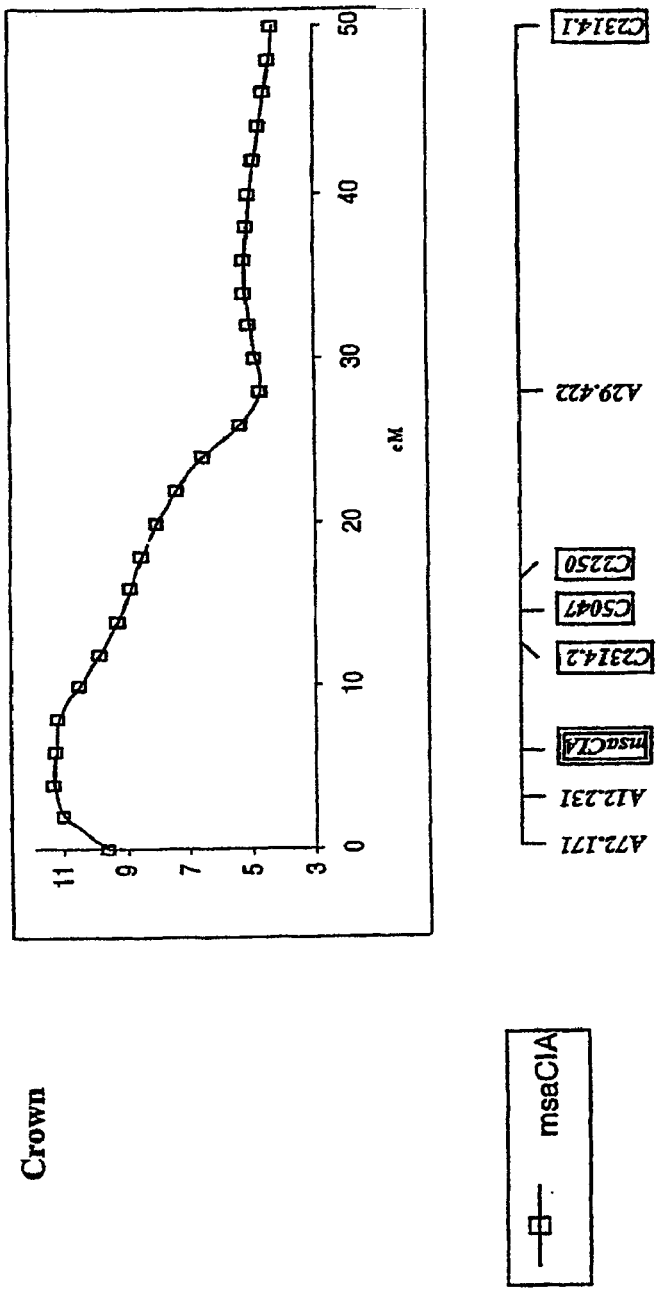
Figure 2 con't

Linkage group E
Crown
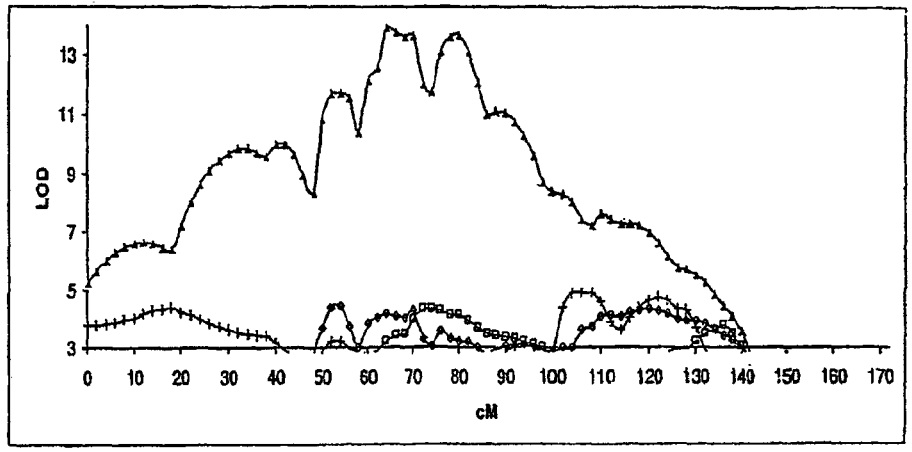
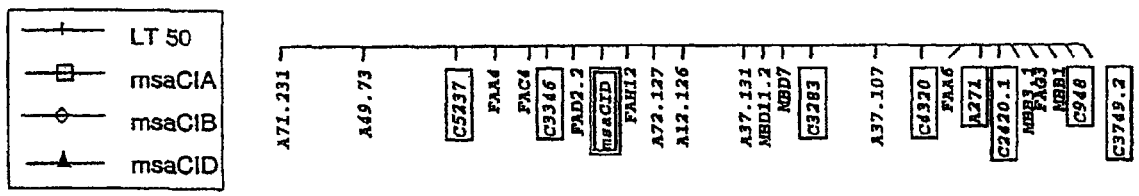
Leaf
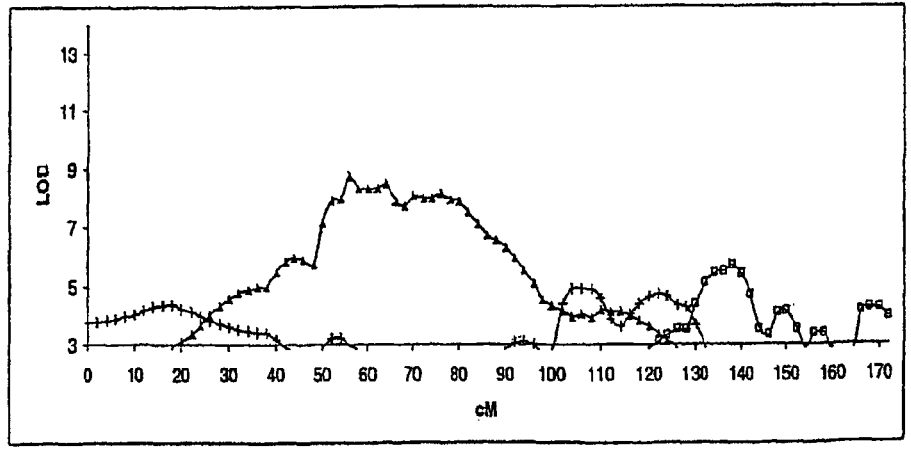
Figure 2 con't

Linkage group F
Crown
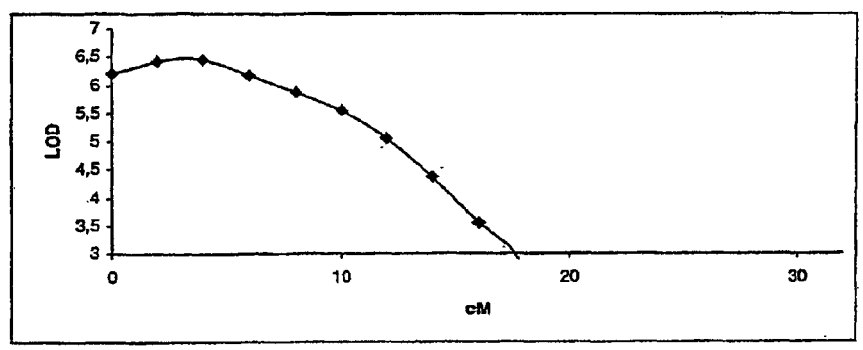
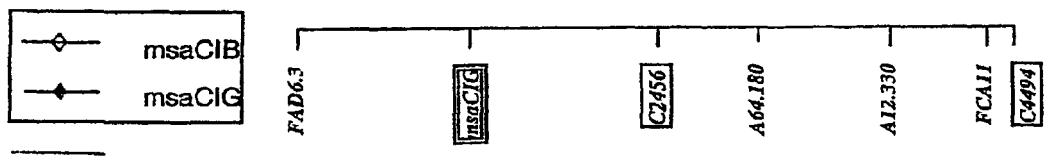
Leaf
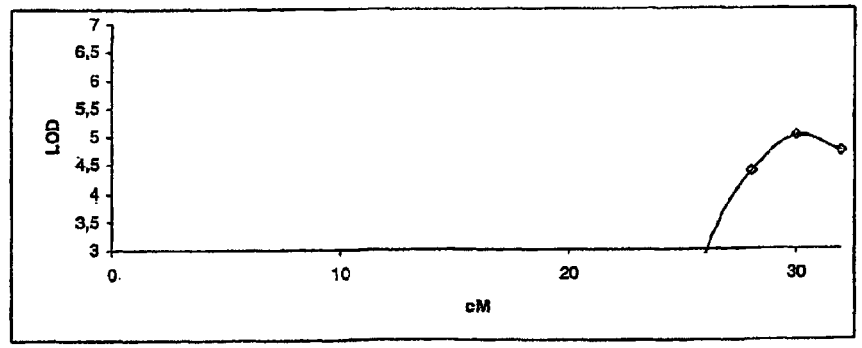
Figure 2 con't

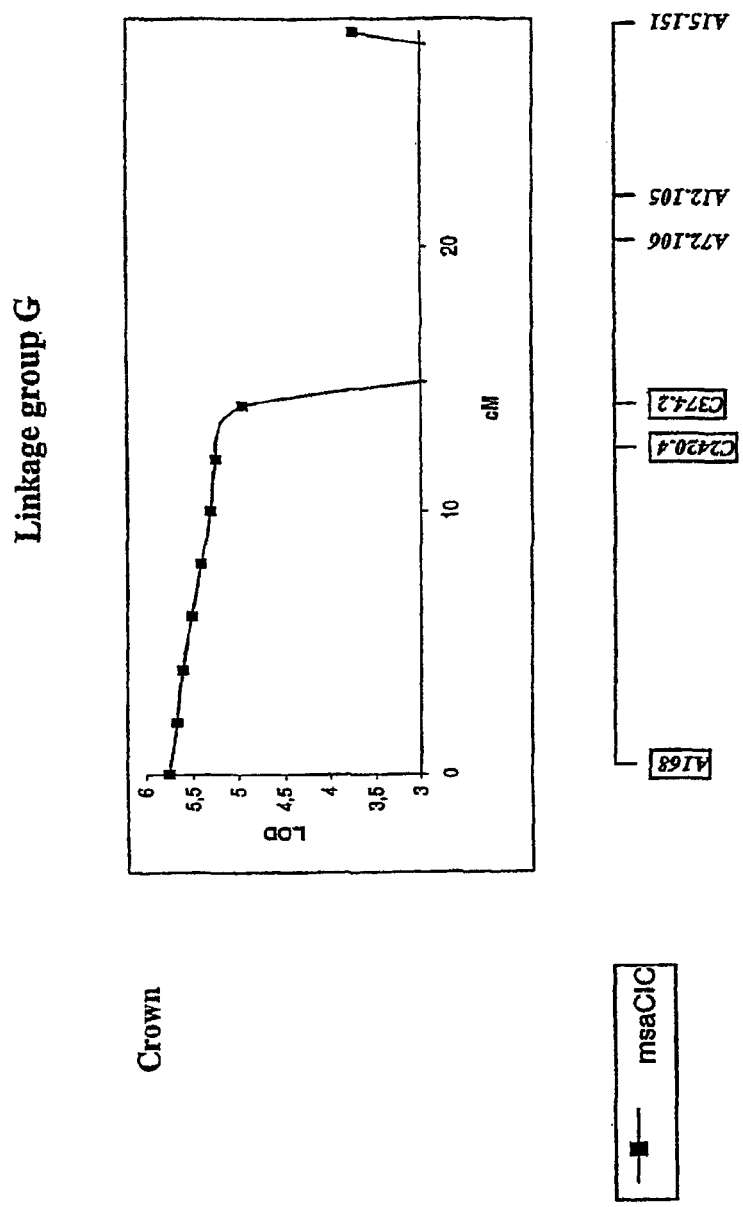
Figure 2 con't

MAP-BASED GENOME MINING METHOD FOR IDENTIFYING REGULATORY LOCI CONTROLLING THE LEVEL OF GENE TRANSCRIPTS AND PRODUCTS

This application is a continuation of U.S. Application Ser. No. 10/333,150, filed May 14, 2003 now abandoned which was a 371 of PCT/CA01/01028, filed Jul. 17, 2001, which claimed the benefit of Provisional Application Ser. No. 60/218,765, filed Jul. 17, 2000, each is incorporated herein by reference in its entirety.

The present invention relates to a method for the identification of regulatory loci that control gene expression within any organism. More specifically, the present invention relates to the use of mRNA transcripts, and variation in transcript levels for the identification of quantitative trait loci pertaining to a desired trait within an organism.

BACKGROUND OF THE INVENTION

The selection of desired plant traits within plant breeding programs is typically based upon selection of one or more phenotypic traits. However, many important agronomic traits are complex, dramatically influenced by the environment, and are under polygenic control where a phenotypic trait is regulated by a plurality of genes, rather than by a single locus control. In traits under polygenic, or multigene control, the expression of alleles at many loci may contribute to the phenotype of interest.

Repeatedly, it has been shown that many genes fail to be expressed in response to developmental or environmental cues. An understanding of the factors that control the expression of these genes is important especially within transgenic organisms, for example, upon the introduction of a foreign gene to control its transcript level in a developmental, tissue or stress dependant manner. Such studies reveal the complexity and multi-level redundancy of controls that exist in the expression of genes. Mechanisms of control of gene expression can vary considerably between genes (see for example Hirt H. 1999 Trends Plant Sci. 4: 7-8). Under a given set of environmental or developmental conditions, genes involved in a given process do not always respond in a similar manner, nor do they accumulate in the same cell types or tissues indicating that they respond to different control or signal mechanisms.

Using current techniques, it is difficult to sort out key regulatory genes that control the expression of genes of interest among the whole cascade of events. Differentially expressed genes have been identified using approaches such as differential screening of cDNA libraries, genome sequencing combined with homology searches in gene banks, gene knock-out and complementation, mutation of homeotic genes, high throughput screening of ESTs using high density arrays of genes. These approaches, even though laborious, have occasionally been useful to identify genes involved in the regulation of gene expression but are not specifically designed for that purpose. Gene knock-out approaches (mutant variation) for the identification of factors controlling gene expression are suitable to small genome species such as Arabidopsis. Such techniques are also laborious, unspecific and often lead to undetectable or lethal phenotypes. Combination of techniques such as differential display of mRNA species, subtractive or normalized libraries and gene array can be used to single out regulatory genes, however these techniques are not specific to the analysis of the expression of a single gene and are time consuming. Moreover, with these techniques the transcripts of the regulatory genes of interest must be present in samples used to generate the libraries in order for the transcripts to be identified. The task can be overwhelming when multiple regulatory genes, with unsynchronised expression axe involved.

A quantitative trait locus (QTL) is a region of the genome that codes for one or more proteins and that explains a significant proportion of the variability of a given phenotype that may be controlled by multiple genes. Typically, one or more genetic markers have been used to identify a desired QTL. To date, most QTL studies of plant species have looked at gross morphological or agronomic phenotypes (e.g. yield, disease and stress resistance, time to flowering etc.). For instance, in WO 2000/18963 soybean plants comprising QTL associated with enhanced yields, and methods for selecting and breeding those plants is disclosed. This method involved the use of a specific marker nucleic acid capable of hybridizing to a second nucleic acid molecule that maps to specific region of Glycine soja and that is associated with enhanced yield. In U.S. Pat. No. 5,948,953 a QTL associated with brown stem rot (BSR) resistance in a soybean plant was identified. The QTL associated with BSR resistance may be used for plant selection using marker assisted selection. WO 99/31964 discloses the use of a marker nucleic acid that is genetically linked to a set of 63 specified loci for plant selection. The identified polymorphisms may be used in DNA fingerprinting and for mapping genes or QTLs associated with pest or disease resistance. Several recent QTL studies have explored the relationship between quantitative variation in specific metabolic changes including metabolite accumulation or changes in enzyme activities. For example, Byrne et al (Byrne, P. F., McCulen, M. D., Snook, M. B., Musket, T. A., Theuri, J. M., Widstrom, N. W., Wiseman, B. R. and E. H. Coe. 1996. Proc. Natl. Acad. Sci. 93: 8820-8825) disclose the mapping of a QTL accounting for 58% of the variance of the concentration of maysin, a flavone acting as a host-plant resistance factor against the corn earworm, to a locus encoding a transcription activator for portions of the flavonoid pathway. Prioul et al. (Priori, J.-L., Quarrie, S., Causse, M. and D. de Vienne. 1997. J. Exp. Bot. 48: 1151-1163; Prioul, J.-L., Pelleschi, S., Séne M., Thévenot, C, Causse, M, de Vienne, D. and A. Leonardi. 1999. J. Exp. Bot 50: 1281-1288) used enzyme activities, substrate and product levels of known biosynthetic pathway as quantitative traits in QTL analysis. Similarly, Pelleschi et al. (Pelleschi. S., Guy, S., Kim, J.-Y., Pointe, C., Mahé, A., Barthes, L., Leonardi, A., and J.-L. Prioul. 1999. Plant Mol. Biol. 39: 373-380) disclose the use of invertase activity as a marker for the identification of candidate genes for QTLs associated with variation in invertase activity in maize. Damerval et al. (Damerval C, Maurice, A., Josse, J. M, and D. de Vienne. 1994. Genetics 137: 289-201) discloses the use of peptides on a 2D-gel as a quantitative trait for QTL mapping.

None of the above approaches demonstrate or suggest that a QTL mapping approach can be used to identify genes involved in the regulation of expression of single genes or cascades of genes, nor do they suggest the use of using mRNA transcripts as the phenotypic trait for QTL mapping.

Dumas et al. (Dumas p., Sun Y., Corbeil G., Tremblay S., Pausova Z., Kren V., Krenova D., Pravenec M, Hamet P., and J. Tremblay 2000, J. Hypertens 18:545-551) disclose the use of mRNA as a phenotypic marker to map QTL associated with stress gene expression in rat. A related approach, using differential gene expression to map QTL associated with blood pressure in rats, was proposed by Cicila and Lee (Cicila G T. and S J Lee 1998 Hypertens Res 21: 289-296). Neither of these papers suggests a QTL approach for the identification of genes that are involved in the regulation of single genes or complex regulatory cascades responsible for controlling transcript levels. Furthermore, there is no discussion of QTL mapping of differential gene expression in organisms characterized as having a ploidy level greater than diploid, nor is there any discussion of identifying QTLs associated with differential gene expression in non-animal hosts.

The present invention is directed to the identification of genomic regions involved in the genetic regulation of the expression of one or more genes of interest associated with a desired trait. By using a QTL map-based analysis of the genome, loci for regulatory genes associated with the differential accumulation of transcripts or gene products are identified.

It is an object of the invention to overcome disadvantages of the prior art.

The above object is met by the combinations of features of the main claims, the sub-claims disclose further advantageous embodiments of the invention.

SUMMARY OF THE INVENTION

The present invention relates to the use of mRNA transcripts, aid variation in transcript levels for the identification of quantitative trait loci pertaining to a desired trait within an organism. More specifically, the present invention relates to a method for the identification of loci for regulatory genes that control gene expression for a given trait within any organism. Finally, the present invention relates to a method for the identification of genes and gene sequences that regulate expression of genes and regulatory cascades controlling expressional traits within the organism.

According to the present invention there is provided a method for identifying one or more regions within a genome of an organism of interest mat mediate the expression of one or more genes of interest comprising:
  i) identifying a first organism of interest characterized in that first organism of interest exhibits a measurable response to an environmental stimulus, or otherwise exhibits a phenotype associated with differential gene expression associated with a process of interest;
  ii) identifying a second organism of interest characterized in that the second organism of interest;
    a) lacks or does not exhibit as strong a response to the stimulus as that of the first organism of interest;
    b) exhibits a different phenotype compared with that of the first organism of interest, the different phenotype associated with the process of interest;
    c) exhibits a phenotype of interest that segregates in a population resulting from a cross with the first organism of interest;
    d) or a combination of two or more of a), b) c) and d);
  iii) crossing the first and second organisms of interest to produce a population of segregated progeny;
  iv) extracting RNA from each of the segregated progeny and quantifying the level of gene expression of one or more genes of interest, the one or more genes of interest associated with the response to an environmental stimulus, or the process of interest;
  v) preparing a linkage map of the segregated progeny using one or more markers;
  vi) determining a relationship between the one or more markers on the linkage map and the gene expression of the one or more genes of interest and identifying one or more quantitative trait loci (QTL).

The present invention also includes the method as defined as above, wherein after the step of crossing (step iii)), and prior to the step of extracting RNA, the segregated progeny are subjected to a desired environmental stimulus or are characterized as being at a specific developmental stage.

The method of the present invention as described above may be used for the identification of one or more QTLs corresponding to a transcription factor or any factor controlling the expression of the one or more genes of interest.

Furthermore, this invention pertains to the method as described above wherein after the step of determining (step vi)), one or more genes located at the one or more QTL are isolated and characterized.

The present invention is also directed to the method as described above wherein in the step of determining (step vi)), a marker is identified at the QTL. Furthermore, the marker may be used for.
  tracing progeny of an organism;
  determining hybridity of an organism;
  identifying a variation of linked phenotypic trait, expression trait, or both phenotypic trait and expression trait;
  construction of a genetic map;
  identifying individual progeny from a cross;
  isolating a genomic DNA sequence surrounding a gene-coding or non-coding DNA sequence; and
  marker-assisted selection, map-based cloning, hybrid certification, fingerprinting, genotyping, as an allele specific marker, or a combination thereof.

The present invention also embraces a method (B) for identifying a regulatory gene that mediates the expression of a gene of interest comprising:
  i) identifying one or more Quantitative Trait Loci (QTLs) that explain a significant proportion of variation of expression of one or more genes of interest;
  ii) mapping the one or more regulatory genes;
  iii) determining whether the one or more regulatory genes map within the one or more QTLs;
  iv) isolating one or more regulatory genes within the one or more QTLs.
  v) sequencing the one or more regulatory genes isolated in step iv).

This invention also includes a method of mediating the response of an organism of interest to an environmental stimulus comprising, transforming the organism of interest with a regulatory gene identified using the method (B) as described above.

Further, this invention realtes a method of mediating development of the organism of interest comprising, transforming the organism of interest with a regulatory gene identified using the method (B) as described above.

The present invention also embraces a method (C) for identifying a regulatory sequence that mediates the expression of a gene of interest comprising:
  i) identifying one or more Quantitative Trait Loci (QTL) that explain a significant proportion of variation of expression of one or more genes of interest;
  ii) mapping the one or more regulatory genes;
  iii) determining whether the one or more regulatory genes maps within the one or more QTL;
  iv) isolating one or more regulatory genes within the one or more QTL; and
  v) sequencing the regulatory sequence of the one or more regulatory genes isolated in step iv).

This invention pertains to a method of mediating the response of an organism of interest to an environmental stimulus comprising, transforming the organism of interest with a regulatory sequence fused to a gene of interest, the regulatory sequence being identified using the method (C) as described above.

Further, this invention includes a method of mediating development of the organism of interest comprising, transforming the organism of interest with a regulatory sequence fused to a gene of interest, the regulatory sequence being identified using the method (C) as described above.

The present method allows the identification of genes that share common regulatory loci or that are under the same regulation. This may have important implications for many claimed applications, for example, but not limited to marker-assisted selection, phenotyping, pathway mapping cascade analysis, gene regulation interaction, gene flux analysis etc.

Genomic regions associated with the level of expression of genes can be identified using QTL mapping analysis. This approach, using gene expression level as a quantitative trait permits identifying gene expression control mechanisms by narrowing the search for such regulatory genes and regulatory sequences to specific genomic regions. The significant QTLs identified herein, and the unexpected high level of variance that they explain indicate the potential of using QTL analysis of gene expression to locate important regulatory factors responsible for stress-induced gene expression. Comparative QTL analysis of multiple genes induced by the same external stimulus further permits the elucidation of complex pathways regulating gene expression and to regroup genes that share regulatory factors.

The technique of the present invention is applicable to genes of interest whose expression is regulated by any factors using a population segregating for levels of expression of such genes. It will allow for the identification of genomic regions. Once identified, these genomic regions can be used to characterize a given genotype without environmental or developmental interferences inherent to techniques based on gene expression.

By identifying one or more QTLs for polygenic traits that are induced by environmental stimulus (for example, but not limited to, temperature stress) or that are related to a given process (for example but not limited to yield determination), the technique of the present invention may also identify one or more QTLs that are commonly related to the phenotypic trait being analysed and the expression of genes of important adaptative value for that given trait. Regulatory genes and regulatory sequences found within these loci are likely to be of important value for the improvement of the polygenic trait.

It is to be understood that the technique of the present invention is applicable to any host organism, however, there are several organisms, for example, but not limited to, unicellular organisms or plants that offer unique advantages over other eukaryotic systems with regard to the application of the technique of the present invention. For example, in some plant species, the generation of doubled haploids from pollen in which every locus is homozygous, the selfing or backcrossing to one or other parental lines of F1s to generate segregating F2 or backcross populations, the possibility to repeatedly self-pollinate individual F2 plants for several generations (F6-F10) to produce a series of recombinant inbred lines, the possibility to multiply every genotype by clonal propagation allows multiple destructive analyses of the same genetic material, and the possibility to submit genetically identical material to various environmental stimuli or other process. Furthermore, these types of clonal material can be replicated in various environmental conditions where genotype, environment or both genotype and environment interaction effect on the phenotype can be studied.

This summary of the invention does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein.

DESCRIPTION OF PREFERRED EMBODIMENT

The present invention relates to a method for the identification of regulatory loci mat control gene expression within any organism. More specifically, the present invention relates to the use of mRNA transcripts, and variation in transcript levels for the identification of quantitative trait loci pertaining to a desired trait within an organism.

The following description is of a preferred embodiment by way of example only and without limitation to the combination of features necessary for carrying the invention into effect.

A quantitative trait locus (QTL) is a region of the genome that explains a significant proportion of the variability of a given phenotype controlled by multiple genes, for example, but not limited to, traits associated with increased yield, freezing tolerance, drought tolerance and the like. Within these regions are located one or more genes coding for factors that have a significant effect on the phenotype of the organism.

Figure 1:
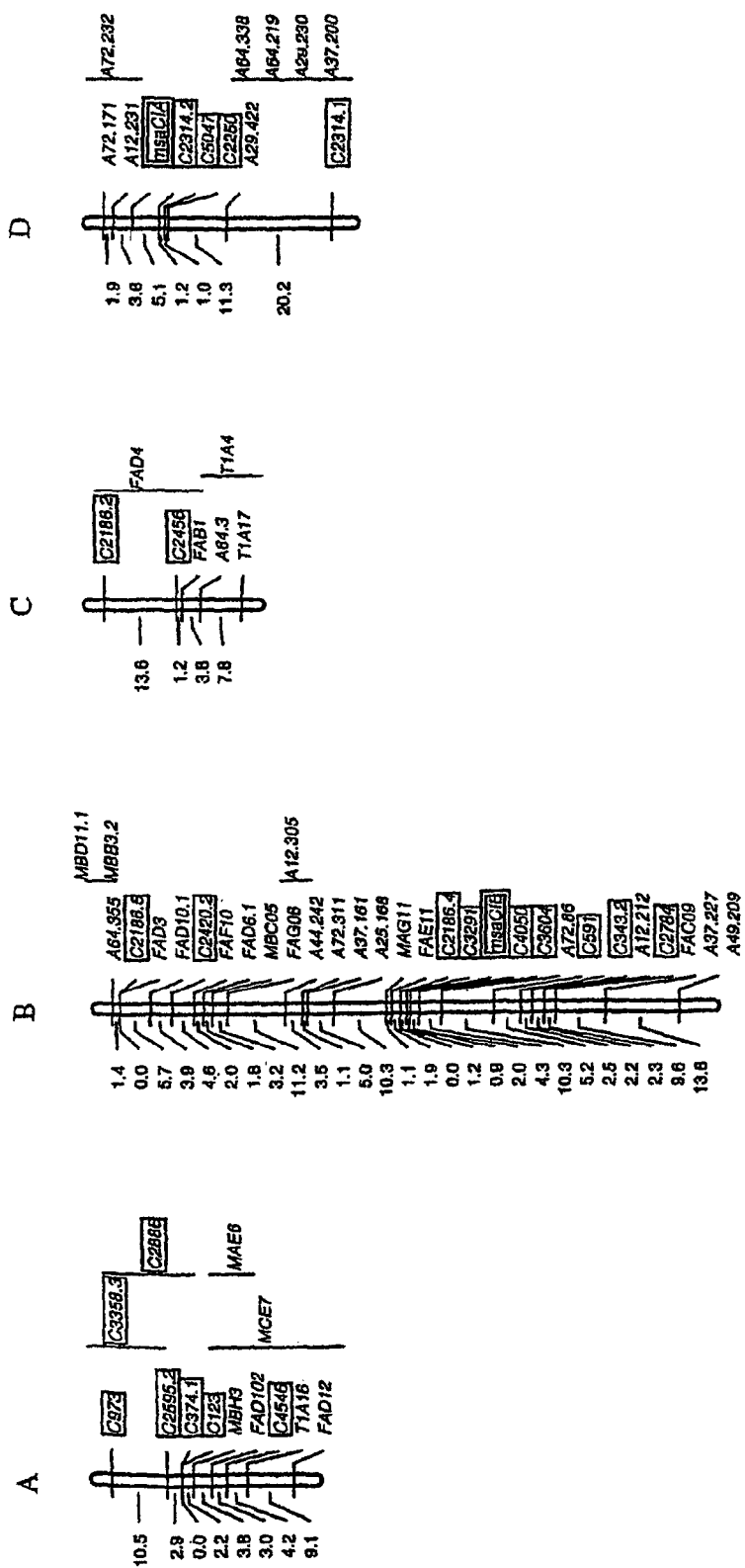
FIG. 1 shows a linkage map of diploid alfalfa. Loci are listed on the right, and recombination distances (cM) are listed on the left of each linkage group. Bars on the right of linkage groups indicate the approximate position of loci. Cold-regulated (msaCI) genes are double framed and genes with homology to genes with regulatory function are framed. Genes that are members of multigene families are numerically distinguished, for example C3358.1 and C3358.3.

As described herein, a linkage map constructed using any type of marker such as morphological, isozyme or DNA based markers may be used to locate each gene of interest to a given location on the map. The expression of a single gene of interest is considered as a quantitative trait. Without wishing to be bound by theory, if the variability of the expression of the gene of interest is the result of differences in the gene itself, for example, due to various allelic forms of the gene, then a major quantitative trait locus should be located close to the location of the structural gene. However, as outlined below, it is observed that the variance of the expression of the gene of interest is highly, and significantly explained by QTLs located elsewhere in the genome (see FIG. 1). Therefore, genomic regions located at a distance from the gene of interest are controlling, or regulating the expression of the gene of interest. These genomic regions may be identified using the linkage map and the regulatory genes that encode factors that control the expression of the gene of interest are then identified using techniques as known to one of skill in the art.

By "gene of interest", it is meant one or more known genes that may be used as a quantitative trait that is being characterized using the method of the present invention, and may include upstream and down stream regulatory regions, introns, and exons. A gene of interest is typically, but not always, expressed under conditions used to determine the effect of regulatory genes on the expression, or suppression, of the gene of interest. The level of expression of the gene of interest may be determined using any methods known in the art, for example, Northern analysis, RNase protection, array analysis, PCR and the like. The gene of interest or the level of its transcripts, is a quantitative trait that is used for further identification of one or more QTLs associated with the expression of the gene of interest. One or more genes of interest may be used within the method of the present invention for the analysis of a response to an environmental stimulus or other process of interest as defined herein. By increasing the number of genes of interest used within the analysis, it is possible to identify one or more QTLs mat axe responsible for the regulation of several genes of interest associated with the response to the environmental stimulus or other process of interest within the plant, possibly highlighting the importance of the QTLs. Such an approach is disclosed below and in the Examples.

By "regulatory gene", it is meant a gene whose product directly or indirectly effects the expression of a gene of interest, and includes the coding region, upstream (5') and downstream (3') non-grading and regulatory regions, and introns. Typically, a regulatory gene is differentially expressed, in response to a stimulus, for example but not limited to, an environmental stimulus such as heat shock or temperature stress. An example of a regulatory gene includes, but is not limited to, a gene that encodes a transcriptional factor, or a gene that encodes another protein factor that in some manner regulates the expression of another gene. The product encoded by a regulatory gene may directly effect the expression of a gene of interest, for example which is not intended to be limiting in any manner, by binding regulatory regions upstream (5') or downstream (3') of the coding region of the gene of interest, or within introns, as is known in the art, and enhancing or silencing the expression of the gene of interest. A regulatory gene may also encode a product mat effects either the stability of the transcript of the gene of interest, the rate or stability of translation or the transcript synthesized from the gene of interest, or both post transcriptional and post translational events pertaining to the expression of the gene of interest. It is also contemplated that a regulatory gene may effect the differential expression of a gene of interest indirectly, by mediating the expression of one or more secondary genes, whose products may then interact with the expression of the gene of interest. It is also contemplated that one or more regulatory genes may act synergistically to mediate the differential expression of a gene of interest.

The method of the present invention allows for the identification of genes that share common regulatory loci or that are under the same regulation. This may have important implications for many applications, for example, but not limited to marker assisted selection, phenotyping, pathway mapping cascade analysis, gene regulation interaction, gene flux analysis, or the identification of regulatory genes having significant effects on polygenic traits By "environmental stimulus" it is meant any stimulus effecting, and producing a measurable response within an organism of interest. For example, which is not intended to be limiting in any manner, the organism of interest may be a plant, plant organ, tissue or cell, and the environmental stimulus may be, for example but not limited to, biotic stimuli including infestation by a virus, bacteria, fungi, insect nematode or other herbivore, or an abiotic stimuli, for example but not limited to, a stress associated with chilling, freezing, water, drought, osmotic, heat, salt, oxidative, or pollutant. An environmental stimulus may also include the effects of mineral nutrition, light, and endogenous or exogenous chemicals on organism of interest or an organ, tissue or cell thereof.

By "process of interest" it is meant any process that produces a measurable effect within an organism of interest or an organ, tissue, or cell thereof, for example, which is not to be considered limiting in any manner, a plant. A process of interest may include but is not limited to, developmental, chemical or environmental control of gene expression during, in the non-limiting case of a plant embryogenesis, flower, seed, root or leaf development, organogenesis, or circadian, ultradian and other internal rhythms. Other processes of interest may include but are not limited to, harvestable yield, photosynthate translocation, sink and source, leaf area index, root shoot ratio, nutritive value of harvested material, plant morphology, rate of cell cycle, rate of cell differentiation, cell size, plant life cycle, senescence, maturation, dormancy, germination, or genomic rearrangements, for example, due to transposon activation. However, it is to be understood that analogous or other unique processes may be characterized using the methods described herein, within any organism of interest.

By, "an organism of interest" it is meant any organism within which one or more QTLs are to be identified and characterized, for example but not limited to a plant (algae, bryophytes, ferns, angiosperm, or gymnosperm), an animal, a unicellular organism, bacteria, phytoplankton, yeast fungi, and also includes cell or tissue cultures of these organisms.

The method of the present invention may be used to identify the level of transcripts of a gene that maps to a specific location in the genome and to determine whether the accumulation of the encoded transcript, or protein, is regulated by genes located at loci elsewhere in the genome. Using a QTL (quantitative trait loci) map-based analysis of the genome, it is possible to identify loci associated with the differential accumulation of transcripts or gene products. Therefore genes found within these QTLs could encode for members of multigene families under different transcriptional controls (for example, harbouring important cis-regulating sequences which in turn influence the regulation of transcription or act on upstream or downstream sequences required fee enhanced translation or mRNA stability), transcription factors (including enhancer and repressors), signal transduction pathway proteins (for example, protein kinases, protein phosphatases, 14-3-3 proteins etc.), external signals receptors, proteins involved in the regulation of secondary messenger levels ($Ca^{2+}$, $IP_3$, cAMP, etc.), nucleases involved in the degradation of transcripts, proteases and proteases inhibitors, novel transcription regulating factors.

An example of the approach used for identifying regulatory genes that control, mediate, or influence, the expression of one or more genes of interest for example, but not limited to, differential expression in response to ah environmental stimulus, or any event within an organism of interest that results in differential gene expression, involves:

i) identifying a first parent organism of interest, that exhibits a response to an environmental stimulus, or otherwise exhibits a phenotype associated with differential gene expression associated with a process of interest, and a second parent organism of interest that lacks or that does not exhibit as strong a response to the stimulus, or exhibits a different phenotype associated with differential gene expression associated with the process of interest, whether or not this variation is found in nature or induced by gene mutation, germ disruption, or gene insertion. It is desired, but not necessary, mat the first and second parents differ in their response to the stimulus, or in differential gene expression associated with the process of interest as long as the response to the stimulus, or in differential gene expression, segregates in the progeny;

ii) crossing the first and second parents to produce a population of segregating progeny. Population types can include, but are not restricted to, F1 (from heterozygous parents), F2, or F3 families, Recombinant Inbred lines, Doubled Haploids, Backcross lines, Testcross lines, and gymnosperm segregating megagametophytes;

iii) if required, subjecting the progeny of this cross to a desired environmental stimulus;

iv) extracting RNA from one or more organs, tissues or cell type, for example, in the case of a plant as an organism of interest, RNA may be obtained from flower, primordia, leaf, stem or root tissues, or cells;

v) measuring the transcript levels of one or more genes of interest using any suitable method, for example but not limited to, dot blot or Northern hybridization, array analysis, or quantitative PCR, array analysis and quantifying the level of gene expression for each progeny;

vi) preparing a genetic linkage map of the segregating population using any appropriate method, for example but not limited to, the use of DNA based markers such as, RFLP (Restriction Fragment Length Polymorphism), AFLP (Amplified Fragment Length Polymorphism), RAPD (Random Amplified Polymorphic DNA), microsatellites, IMP (Inter MITE polymorphism), or SNPs (Single Nucleotide Polymorphism), protein markers, or morphological markers to characterize the individuals of the mapping population and subjecting the data obtained from one or more of these techniques to obtain two-point and multi-point linkage analysis for the construction of the linkage map;

vii) determining the relationship between markers on the linkage map and the expression of the one or more genes of interest in response to the environmental stimulus, or associated with a process of interest, to identify statistically significant QTLs. Such a relationship may be determined using any method known to one of skill in the art, for example, but not limited to, single point ANOVAs, simple regression, Interval mapping, Composite interval mapping. Such an analysis may be performed using MAPMAKER/QTL, MQTL, QTL Cartographer, or other similar software. The statistical significance and percent of variance far each QTL are also calculated.

The method as described herein provides an effective method for the exhaustive identification of many, if not all, the regulatory factors (genes) involved in the control of the expression of a gene of interest, and provides an estimate of the relative contribution of each factors to the observed variability of expression of the gene of interest, as well as identifying the regulatory gene's genomic location and associated markers which can be used in traditional plant breeding. In addition, "master switch" regulatory genes affecting the expression of many genes, for example within a cascade, can be identified when multiple genes induced by a given environmental stimulus or mat are related to a given process are analysed simultaneously.

Once one or more QTLs have been identified that are significantly associated with the expression of the gene of interest, then each of these loci and linked markers may be used either directly as markers, for example, but not limited to breeding and screening purposes, including plant breeding, or further characterized to determine the gene or genes involved with the expression of the gene of interest, using map-based cloning methods as would be known to one of skill in the art. For example one or more known regulatory genes can be mapped to determine if the genetic location of these genes coincide with the QTLs controlling mRNA expression of the gene of interest. Confirmation that such a coinciding regulatory gene is effecting the expression of one or more genes of interest can be obtained using standard techniques in the art, for example, but not limited to, genetic transformation, gene complementation or gene knock-out techniques, or overexpression. The genetic linkage map can also be used to isolate the regulatory gene, including any novel regulatory genes, via map-based cloning approaches that are known within the art whereby the markers positioned at the QTL are used to walk to the gene of interest using contigs of large insert genomic clones. Positional cloning is one such a method that may be used to isolate one or more regulatory genes as described in Martin et al. (Martin, G. B., Brommonschenkel, S. H., Chungwongse, J., Frary, A., Ganal, M. W., Spivey, R., Wu, T. Earle, E. D. and S. D. Tanksley, 1993, Science 262: 1432-1436; which is incorporated herein by reference), however, other suitable methods may also be used as recognized by one of skill in the art. Again confirmation that such a coinciding regulatory gene is effecting the expression of one or more genes of interest can be obtained via genetic transformation and complementation or via knock-out techniques described below.

Therefore, the present invention is directed to identifying regions within the genome of a plant that are involved in mediating the expression of one or more genes of interest in response to an environmental stimulus, or a process associated with differential gene expression within a process of interest. The present invention is also directed to characterizing the identified QTL to identify the one or more regulatory genes and regulatory sequences at these loci.

The method of the present invention may also be used to identify loci corresponding to factors (encoded by regulatory genes) associated with the control or mediation of expression of a gene of interest in an organism of interest. This method can be used for the identification of regulatory genes that control and modulate the level of mRNA transcripts of one or more genes of interest whether or not this variation is found in nature or induced by gene mutation, gene disruption, or gene insertion, for example, but not limited to, genes of interest that are regulated by factors involved in:

biotic stresses, for example but not limited to virus, bacteria, fungi, insects, or nematodes;

abiotic stresses including but not limited to chilling, freezing, water, drought, osmotic, heat, salt, oxidative, pollutants;

developmentally, chemically and environmentally controlled gene expression;

embryogenesis, for example, but not limited to tissue, or organ development, which in the case of a plant may include seed development, organogenesis, floral development;

mineral nutrition, including both macro and micro nutrients;

light (irradiance level and light quality);
circadian, ultradian and other internal rhythms;
chemical inducers including natural growth regulators, for example, in the case of a plant being the organism of interest, auxins, gibberellins, ABA, cytokinins, ethylene, and their analogs, synthetic hormones, herbicides, salicylic acid, jasmonic acid;

or genes of interest that have a significant impact on biological processes such as:
the determination of yield, for example which is not to be considered limiting, in plants, determination of harvestable yield, through the effects of regulatory genes on biomass, seed setting (number and size), photosynthate translocation, sink and source, leaf area index, root shoot ratio;
nutritive value of biomass, for example but not limited to, harvested material and associated effects on the levels of quality factors such as cofactors, vitamins, proteins, antioxidants, highly digestible fibers;
morphology, for example, but not limited, in plants, to the effect of regulatory genes on flower color (e.g. genes involved in anthocyanins synthesis), plant height (e.g genes involved in gibberellins synthesis), internode length, leaf insertion;
rate of cell cycle, for example but not limited to cyclins;
rate of cell differentiation, for example but not limited to homeodomain proteins;
cell size, for example but not limited to, in plants, to genes involved in auxin synthesis, auxin receptors, auxin-induced genes;
organism life cycle, for example through the effect of regulatory genes on senescence, maturation, dormancy, germination;
genomic rearrangements, for example, transposon activation;

In addition to using the method of the present invention to identify loci corresponding to transcription, or any factors controlling the expression of genes in an organism of interest for various desired traits, the markers located in these QTL may also be used in applied breeding. For example, identified polymorphisms associated with one or more identified genetic markers located at a locus (a QTL) may be used: for genome-based diagnostic and selection techniques:
for tracing progeny of an organism;
to determine hybridity of an organism;
to identify variation of linked phenotypic traits, mRNA expression traits, or both phenotypic and mRNA expression traits;
as genetic markers for constructing genetic linkage maps;
to identify individual progeny from a cross wherein the progeny have a desired genetic contribution from a parental donor, recipient parent, or both parental donor and recipient parent;
to isolate genomic DNA sequence surrounding a gene-coding or non-coding DNA sequence, for example, but not limited to a promoter or a regulatory sequence;
in marker-assisted selection, map-based cloning, hybrid certification, fingerprinting, genotyping and allele specific marker; and
as a marker in an organism of interest.

Using a QTL map-based analysis described herein, regulatory loci associated with the expression of a gene of interest, at the whole organism, organ, tissue or cell specific level, in response to an environmental stimulus, or a phenotype associated with differential gene expression associated with a process of interest may also be identified. For example, which is not to be considered limiting in any manner, candidate regulatory genes that modulate the expression of mRNA, such as (also see Table 2 Example 2):
Transcription factors (zinc-finger and AP2 proteins);
Mitogen-activated protein kinases (MMK4, MMK3, MMK2, MMK1);
Calcium-dependent protein kinases;
Serine-threonine protein kinase;
$Ca^{2+}$ transporting ATPase;
GTP binding proteins;
RNA binding proteins;
Protein phosphatases (type 2A and 2C);
$Ca^{2+}$-binding proteins, for example Calmodulin;
14-3-3 proteins;
GTPase activating proteins;
Adenylyl cyclase protein;
Phospholipase C;
Lipoxygenase;
Histone deacetylase;
Receptor kinase; or
Phosphatidyl inositol 3-kinase may be evaluated to determine if they map to regions of the genome (QTL) that explain a large proportion of the expression of cold-regulated genes in a plant, for example but not limited to, alfalfa (*Medicago falcata* L.).

The method as described herein may be used to complement high throughput genome analysis studies based on DNA chips and grid arrays, or any other system capable of measuring gene expression. Using segregating populations, it is possible to locate QTLs regulating the transcripts level of genes which expressions is related to phenotypes of interest (e.g stress and disease resistance, biochemical production, morphological variations etc.). Mapping of candidate genes from EST collections establishes potential co-location to important QTLs and allows for the identification of allelic polymorphism and the development of allele-specific markers. The identification of these QTLs, and the associated regulatory genes, may be used for genome-based diagnostic and selection techniques for assessment of gene expression potential under given developmental or environmental conditions and the coordination of gene expression in a developmental, tissue, or environmental manner.

Genomic regions associated with the level of expression of genes, for example, but not limited to those induced by low temperature, can be identified using QTL mapping analysis. This approach, using gene expression level as a quantitative trait permits identifying gene expression control mechanisms by narrowing the search for such regulatory genes to specific genomic regions. DNA sequences responsible for variation in gene expression are also likely to be found within these regions. The gene identification method described herein will become easier and more rapid with the availability of whole genome sequences and the routine integration of increasingly large number of ESTs onto high density maps or by taking advantage of the extensive collinearity of blocks of genes along chromosomes of related species in comparative genetic mapping.

The very significant QTLs identified within the Examples herein, and the unexpected high level of variance that they explain indicates the potential of using QTL analysis of gene expression to locate important regulating factors responsible for stress-induced gene expression. Comparative QTL analysis of multiple genes induced by the same environmental stimulus or that are involved in a given process permits the elucidation of complex pathways regulating gene expression and to regroup genes that share the similar regulation factors.

The technique of the present invention will be applicable to genes which expression is regulated by any factors using a population segregating for levels of expression of such genes. It will allow for the identification of genomic regions that can be used to characterize a given genotype without environmental or developmental interferences inherent to techniques based on gene expression.

In order to identify regulatory genes that may be localized atone or more QTLs that explain a significant proportion of the variation of the expression of one or more genes of interest, probes are obtained from known regulatory genes, for example, but not limited to the regulatory genes listed above, and in Table 2 of Example 2, and these regulatory genes, or their expression products are mapped on a linkage map. These probes may include nucleotide fragments or full-length genes for the detection of DNA or RNA, or antibodies for the detection of the expression products of a regulatory gene. It is to be understood that unknown regulatory genes located at one or more QTLs may also be identified using methods as known to one of skill in the art, for example, but not limited to, positional cloning and mapping portions of the sequenced DNA to determine if the cloned DNA co-locates (maps) with the one or more identified QTLs. Preferably, the location of the candidate regulatory genes at one or more QTLs is confirmed, for example by mapping upstream or downstream regions from each putative regulatory gene on the linkage map. In this manner, only regulatory genes that are characterized by having 5' or 3' regions that co-Locate with the same QTLs are used for further characterization.

Regulatory genes that are located within one or more QTLs that are associated with the expression of one or mere genes of interest may men be isolated and characterized, and their expression modulated within a transgenic plant, for example but not limited to alfalfa, in order to assess their effect on expression of the gene of interest, and if desired, their effect on the response of the organism of interest to an environmental stress. Such analysis may include, but is not limited to, complementation or gene knockout, and gene activation, studies involving transformation of the organism of interest with a sense or antisense construct of the regulatory gene or enhancer sequences, respectively. An organism of interest mat lacks or exhibits a weak response to an environmental stimulus, or a process of interest, is transformed with a sense construct of the regulatory gene, while an organism of interest that exhibits a strong response, or scores positively for process of interest, is transformed with an antisense construct of the regulatory gene, or disrupted by insertion of a foreign DNA such as T-DNA into the coding region of the gene, or activated by insertion of an enhancer sequence 5' or 3' of the gene of interest. Expression of one or more genes of interest and the regulatory gene may then be monitored to determine the effect of the sense, antisense, knockout or enhancer insertion regulatory gene on the organisms response to an environmental stimulus, or on process of interest. The effect of the sense, antisense, knockout or enhancer insertion constructs on a physiological response to an environmental stress may also be determined.

It is also contemplated that a regulatory gene located at a specific QTL, or groups of QTLs, may also be used as a marker for the one or more QTLs within breeding programs.

Therefore this invention also pertains to a method for identifying a regulatory gene that mediates the expression of a gene of interest comprising:
   i) preparing a linkage map of the organism of interest;
   ii) identifying one or more QTLs that explain a significant proportion of the variation of the expression of one or more genes of interest; and
   iii) isolating and mapping one or more regulatory genes to determine if the regulatory gene maps within the identified one or more QTLs.

The present invention is also directed to mediating a response of an organism of interest to an environmental stress, or characterizing the in vivo effect of an identified and isolated regulatory gene, by introducing the regulatory gene into the organism of interest and, optionally, determining the effect of the regulatory gene on the expression of one or more genes of interest, or its effect on the response of an organism of interest to an environmental stimulus.

The above description is not intended to limit the claimed invention in any manner, furthermore, the discussed combination of features might not be absolutely necessary for the inventive solution.

The present invention will be further illustrated in the following examples. However it is to be understood that these examples are for illustrative purposes only, and should not be used to limit the scope of the present invention in any manner.

Example 1

Identifying QTLs Associated with Cold-Regulated Gene Expression

General Description of the Experimental Approach

Expression of cold-regulated (msaCI) genes and $LT_{50}$ phenotypes are used as an example of quantitative traits to be characterized within clonal propagules of $F_2$ genotypes of diploid alfalfa. The segregation patterns of the phenotypes (msaCI genes expression, and $LT_{50}$) are used to search for quantitative trait loci (QTL) on a linkage map of diploid alfalfa genome.

Plant Material

An $F_1$ population is constructed by intercrossing diploid parents exhibiting contrasting cold tolerance (*M. falcata*×*M. sativa*). The $F_1$ line is produced by a cross-pollination between a cold sensitive *M. sativa* genotype from the cultivated alfalfa at the diploid level group (Bingham, E. T. and T. J. McCoy. 1979. Crop Sci 19: 97-100) as the female parent with one hardy diploid genotype from *M. falcata* cv. Anik (Pankiw, P. and Siemens, B. 1976. Can. J. Plant Sci. 56: 203-205) as the male parent. Flowers are emasculated and hand pollinated. One randomly selected genotype of the $F_1$ is selfed by hand pollination and the $F_2$ progeny from this cross is used to produce a linkage map and QTL analysis.

Growth Conditions

Cuttings from 117 $F_2$ genotypes are clonally propagated and transplanted in deep pot inserts after root initiation. Clonal propagules are then grown under environmentally-controlled conditions at 21° C. and 17° C. (day, night respectively) temperatures, with a 16 hour photoperiod at an irradiance of approximately 225 µmol m$^{-2}$ s$^{-1}$ photosynthetic photon flux density.

Cold Acclimation Conditions

Plants are cold acclimated two weeks in a growth chamber at 2° C., with an 8 h photoperiod and an irradiance of approximately 125 µmol m$^{-2}$ s$^{-1}$ photosynthetic photon flux density.

$LT_{50}$ Determination

Clonal propagules of each genotype from the segregating population and parental genotypes are submitted to a freezing test as described by Castonguay et al (Castonguay, Y., Nadeau, P., and S. Laberge 1993. Plant Cell Physiol. 34: 31-38). Plants are subjected to a stepwise decrease in ambient temperature during which time individual plants are retrieved at intervals and allowed to regrow under initial growth conditions (21/17° C., day night temperatures, respectively) for three weeks before assessment of plant survival. The 50% killing temperature ($LT_{50}$) is computed by the SAS™ Probit procedure (Statistical Analysis System, Cary, N.C.). Three replicates of an incomplete block design with cyclic permutations (12 blocks) are performed in order to statistically compare the large number of ecotypes used in the study.

Description of msaCI Genes

Seven msaCI genes isolated from a cDNA library from cold-acclimated crowns of tetraploid alfalfa (*M. sativa* cv. Apica; Laberge, S, Castonguay, Y. and Vézina, L.-P. 1993. Plant Physiol 101, 1411-1412; Castonguay, Y., S. Laberge, P. Nadeau, and L.-P. Vézina, 1997. p. 175-202. In B. D. McKersie and D. W. Brown (ed.). Biotechnology and the improvement of forage legumes. CAB International, Wallingford, UK) are used in this study:

| | | |
|---|---|---|
| msaCIA | Glycine-rich | Laberge et al. (1993)* |
| msaCIB | Putative nuclear protein | Monroy et al. (1993)** |
| msaCIC | Bimodular protein | Castonguay et al. (1994)*** |
| msaCID | Pathogenesis-related protein | Unpublished |
| msaCIE | Glyceraldehyde-3P-dehydrogenase | Unpublished |
| msaCIF | Galactinol synthase | Unpublished |
| msaCIG | Dehydrin-like | Unpublished |

*Laberge, S, Castonguay, Y. and Vézina, L.-P. 1993. Plant Physiol. 101, 1411-1412.
**Monroy, A. F., Castonguay, Y., Laberge, S., Sarhan, F, Vézina, L.-P. and Dhindsa, R. S. 1993. Plant Physiol. 102, 873-879.
***Castonguay, Y., Laberge, S., Nadeau, P. and Vézina, L.-P. 1994. Plant Mol. Biol. 24, 799-804.

RNA Extraction

Approximately 0.5 g (fresh weight) leaf tissue from each cold acclimated genotype is ground to a fine powder in liquid $N_2$ using a mortar and a pestle, and total RNA is extracted using standard methods as previously described (Castonguay et al. 1994. Plant Mol. Biol. 24, 799-804). Total RNA is quantitated by UV absorption at 260 nm (Fourney, R. M., J. Miyakoshi, R. S. Day III and M. C. Paterson. 1988. Focus 10:1).

Dot Blot Quantification

For each parental genotype and each genotype of the segregating population, five μg of total RNA are vacuum-transferred to a nylon membrane (Hybond N+, Amersham Pharmacia Biotech, Oakville, ON) using a Bio-Dot™ apparatus (Bio-Rad, Mississauga, ON) and immobilized by cross-linking under UV light for 3 minutes. Membranes are hybridized overnight at 68° C. in 2×SSC, 0.25% (W/V) low-fat powder milk, 1% SDS with [$^{32}$P]dCTP-labeled probe prepared from purified inserts of cold-regulated genes according to standard protocoles (Sambrook, J., Maniatis, T. and Fritsch. 1989. Molecular cloning: A laboratory manual. Cold Spring Harbor Laboratory Press, Cold Spring Harbor, N.Y.). Membranes are exposed with Kodak X-Omat AR5 X-ray film at −80° C. and transcripts level is quantitated by densitometric analysis of autoradiographs using OneD Scan™ software (Scanalytics inc., Billerica, Mass.). See FIG. 3 for an example of one such dot blot obtained using msaCIA gene as a probe. The mean transcript levels of all samples on each membrane is used to standardize hybridization signal across membranes.

Linkage Map

A genetic linkage map is constructed based on AFLP and RFLP. DNA is extracted from 1-2 g of fresh leaf tissue from 4-6 week-old clonal propagules. The method for extraction is essentially as described by Doyle and Doyle (Doyle, J. J. and Doyle, J. L. 1990. Isolation of plant DNA from fresh tissue. FOCUS 12, 13-15), except that the leaf tissue is ground without liquid nitrogen at room temperature.

To uncover RFLP markers, DNA purified from 169 $F_2$ genotypes is separately digested with restriction enzymes DraI and EcoRV. Each digested DNA sample (6 μg per genotype is separated on horizontal gels (0.9% agarose, 1×TAE), and the separated fragments transferred to nylon membranes (Hybond N+, Amersham Pharmacia Biotech, Oakville, ON) by capillary blotting. Ten duplicate copies of membranes are made for simultaneous segregation analyses with multiple probes. Membranes are hybridized overnight at 65° C. with probes labelled with [$^{32}$P]-dCTP. DNA probes consist of randomly selected cDNAs and cDNAs selected according to their homology to regulatory genes both obtained from *Medicago saliva* cDNA libraries, and the 7 msaCI cDNAs described above. cDNA inserts are first specifically amplified by PCR and labelled by random hexamer labelling using the T7 QuickPrime™ Kit (Amersham Pharmacia Biotech, Oakville, ON). Prehybridization, hybridization, and probe labeling are performed according to standard protocols (Sambrook, J., Maniatis, T. and Fritsch. 1989. Molecular cloning: A laboratory manual. Cold Spring Harbor Laboratory Press, Cold Spring Harbor, N.Y.).

To identify AFLP markers, $F_2$ DNAs are digested with EcoRI and MseI restriction enzymes, ligated to Eco- and Mse-specific primer adapters, then amplified by pre-selective Eco and Mse PCR primers (Vos. P., Hogers, R., Bleeker, M., Reijans, M., van der Lee, T, Homes, M, Frijters, A., Pot, J., Pelerman, J., Kuiper, M, and Zabeau, M. 1995, Nucleic Acids Res. 23, 4407-4414). Pre-selective amplicons are diluted 20-fold to be used as material for selective amplification. Both Eco and Mse primers, used for selective amplification, contained 3 selective nucleotides at the 3'end. The Eco primer is labelled with IRD dyes, which permit the detection of amplicons by the infrared laser of a LI-COR automated sequencer (LI-COR, Inc. Lincoln, Neb, USA). Selective amplification is carried out according to the "touch down" protocol described by Vos et al. (1995, Nucleic Acids Res. 23, 4407-4414). After selective amplification, amplicons were separated on 25 cm gels composed of 7% Long Ranger acrylamide, 7M urea, and 0.6×TBE, using a LI-COR automated DNA sequencer model 4000L.

The genetic map of the diploid cross is constructed using the segregation data from 112 RFLP and 117 AFLP segregating markers. Co-segregation analyses are performed using MAPMAKER/EXP v 3.0 software (Lander, E. S., Green, P., Albertson, J., Barlow, A., Daly, M. J., Lincoln, S. E., and Newburg, L. 1987. Genomics 1, 174-181) to determine the linkage group assignment of each marker and the location of each molecular marker within each linkage group. Individual linkage groups are obtained using two-point analysis with a minimum LOD score of 15 and maximum recombination level of 30%. Multiple point analysis with an LOD threshold of 2.0 is then used to order the loci within the linkage groups. The resulting map (FIG. 1) covers approximately 1400 cM and has an average marker interval of approximately 8 cM. Fifteen markers remained unlinked.

Identification of QTL Associated with msaCI Genes Expression and Freezing Tolerance QTLs involved in msaCI gene expression are identified with MAPMAKER/QTL v 1.1. (Lander, E. S., and Boststein, D. 1989, Genetics 121, 185-199). The linkage map is scanned for the presence of QTLs in specific regions of the genome using the expression of each gene as a quantitative trait. The action of each QTL in relation to each other and the percent of the variance of msaCI gene expression explained by each QTL is determined. An LOD threshold of 2.0 is used for the identification of QTL.

Figure 3:
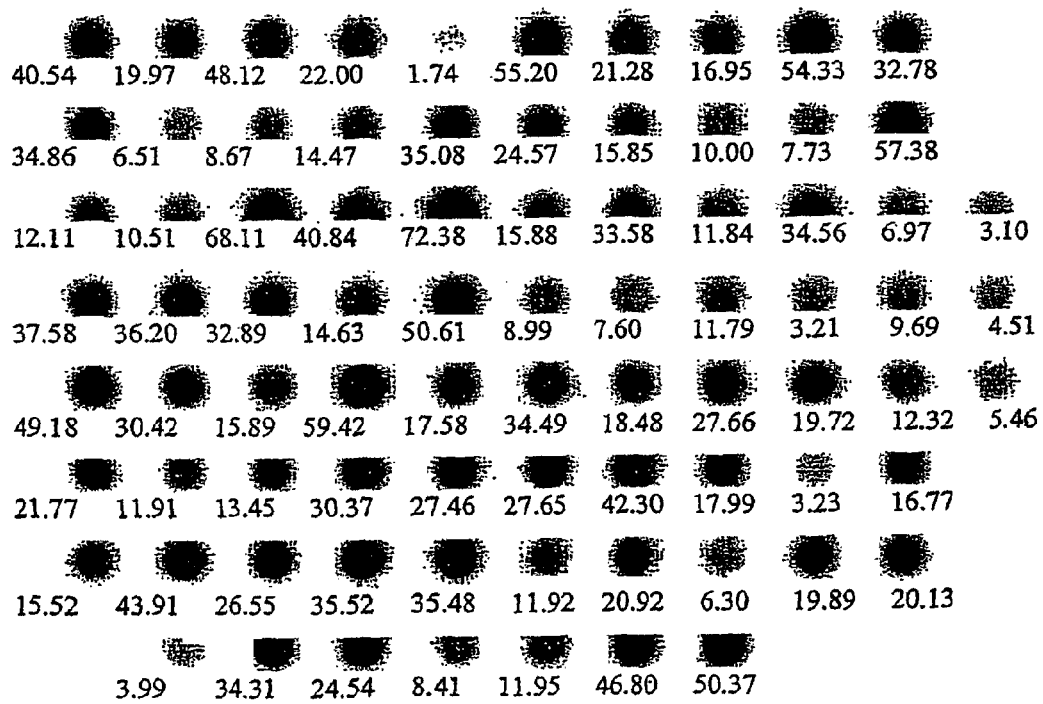
FIG. 3 shows one example of a dot blot analysis of the expression of a gene of interest, in this case the msaCIA gene, in segregating $F_2$ progeny of diploid alfalfa. Each dot corresponds to a unique genotype except for the last column where a control is dotted in triplicate. Level of transcripts are quantified by densitometry and used as a quantitative trait for QTL analysis. Optical density value is indicated for each genotype and the control.

Analysis of cold-regulated accumulation of transcripts for each of the 7 msaCI genes reveals a large genotypic variability for their expression with, in some cases, 10 to 40 fold differences in expression between genotypes (for example see FIG. 3).

QTLs related to the variability of msaCI gene transcript levels observed among genotypes are found for all 7 msaCI genes, and for the $LT_{50}$ phenotype (Table 1). Genes that play an important regulatory role in the expression of msaCI genes are found within these QTLs. The number of QTLs associated with expression of msaCI genes varied from 1 (msaCIF) up to 5 (msaCIC). In most cases their LODs were highly significant. The phenotypic variation explained by these QTLs varied from 10 to 60%. In most cases the increase in expression and frost tolerance, respectively, was due to the allele from the cold tolerant *M. falcata* parent.

Three QTLs relating to freezing tolerance ($LT_{50}$) are identified. Two of these QTLs are located in linkage group in a genomic region associated also with the expression of msaCIB and msaCID.

Figure 2:
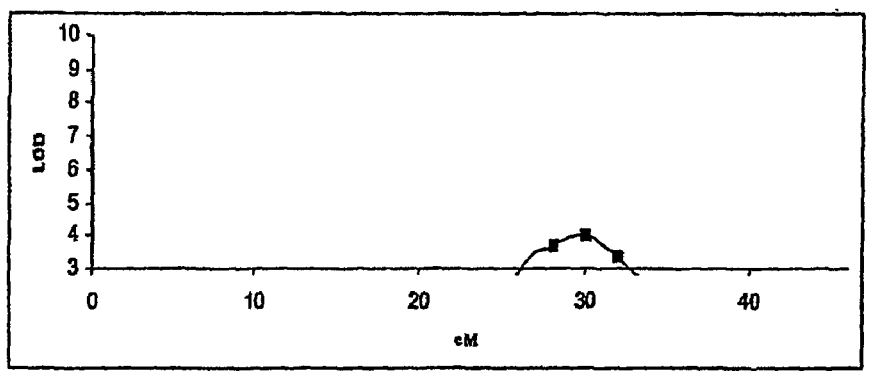
FIG. 2 Position and statistical significance (LOD scores) of QTLs for $LT_{50}$ and cold regulated msaCI gene expression. msaCI genes are double framed and genes with homology to genes with regulatory function are framed. When gene expression QTLs are detected in both crown and leaf tissue, the graph for LOD scores of expression in crown is shown at the top and the graph for LOD scores of expression in leaves is shown at the bottom. $LT_{50}$ QTLs apply to whole plaint and are independent of tissue type. Genes that are members of multigene families are numerically distinguished for example C3358.1 and C3358.3.
Figure 2:
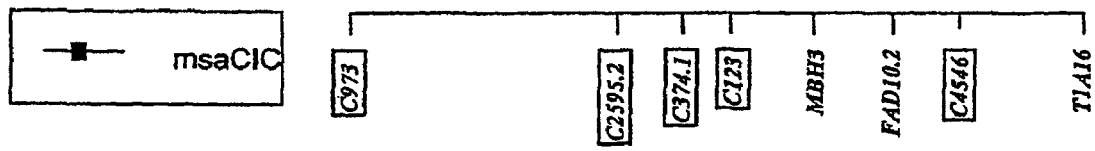
Figure 2:
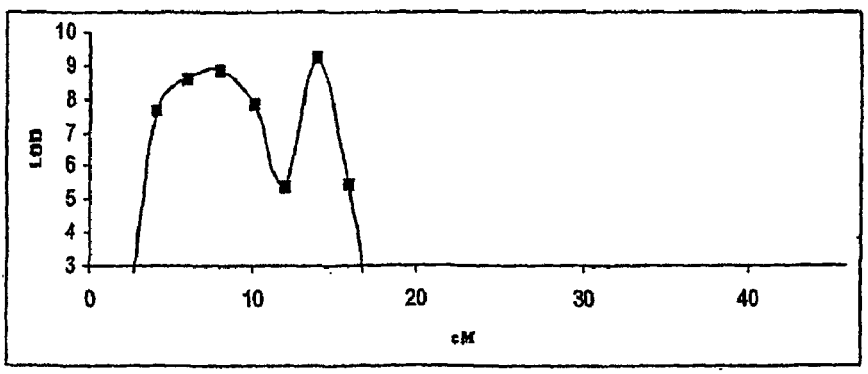

QTLs for the expression of msaCI genes are found associated with the position of the corresponding structural gene for msaCIA (see linkage group D, FIG. 2) msaCID (see linkage group E, FIG. 2) and msaCIG (linkage group F, FIG. 2).

In the case of msaCID the RFLP locus coincides with expression QTLs for three genes; the msaCID gene itself, msaCIA and msaCIB (see Linkage Group E, FIG. 2). This suggests that either msaCID is a regulatory gene or a regulatory gene is located in its vicinity.

QTLs for the expression in crown and leaf tissues that are located in the same genomic region were observed for msaCIA (between 120-130 cm, FIG. 2, Linkage Group E) and msaCID (see linkage group E, FIG. 2). Otherwise the loci affecting the expression in each tissue type were different. QTLs controlling the expression of several msaCI genes are located in linkage groups B and E suggesting a common regulatory mechanism. A particularly striking example is a QTL on linkage group B which has an effect on the expression in leaf tissue of five of the msaCI genes studied (FIG. 2, Table 1).

TABLE 1

QTL associated with the mRNA expression of cold-regulated genes and freezing tolerance in diploid alfalfa. Linkage groups associated with gene expression in leaves or crowns or to freezing tolerance ($LT_{50}$) along with LOD scores are presented. Regulatory genes that map to these genomic regions are identified. The highlighted genes C4494 and C2186 show homology to the CBF1-gene from *Arabidopsis* and the SCOF-1 gene from soybean, respectively, for which an involvement in cold tolerance has been demonstrated.

| Gene/trait | Linkage group Crown | Linkage group Leaf | LOD Crown | LOD Leaf | Candidate regulatory gene Crown | Candidate regulatory gene Leaf | Homology to genes coding for |
|---|---|---|---|---|---|---|---|
| msaCIA |  | B |  | 3 |  | C2784 | Serine/threonine-protein kinase |
|  | D |  | 11 |  | msaCIA |  |  |
|  | D |  | 9 |  | C2314 |  | Phosphatase 2C |
|  | D |  | 9 |  | C5047 |  | Leucine rich repeat (LRR) receptor-like protein kinase |
|  | D |  | 9 |  | C2250 |  | GTP binding protein (Ras-related) |
|  | E |  | 4 |  | msaCID |  |  |
| msaCIB | E | E | 4 | 5 | C4320 | C4320 | Mitogen-activated protein kinase |
|  |  | E |  | 4 |  | C271 | Serine protein kinase |
|  |  | E |  | 4 |  | C948 | Casein kinase I |
|  |  | E |  | 4 |  | C3749 | CDC2+/CDC28-related protein kinase R2 |
|  |  | B |  | 3 |  | — |  |
|  | E |  | 4 |  | msaCID |  |  |
|  | E |  | 4 |  | C3283 |  | Ethanolamine kinase |
| msaCIC |  | F |  | 5 |  | C4494 | AP2 domain transcription factor (CBF1 homolog) |
|  | A |  | 4 |  | C4546 |  | Mitogen activated protein kinase (MAP3K) |
|  |  | A |  | 5 |  | C2595 | Calreticulin |
|  |  | A |  | 5 |  | C374 | Peptidyl-Prolyl cis-trans isomerase |
|  |  | A |  |  |  | C3358 | Adenosine kinase |
|  |  | A |  |  |  | C2886 | Cyclase-associated protein (CAP) |
|  | B |  | 6 |  | — | — |  |
|  |  | B |  | 3 |  |  |  |
|  | G |  | 6 |  | C168 |  | Transcription factor |
|  | G |  | 5 |  | C2420 |  | Ca2+-transporting ATPase-like protein |
|  | G |  | 5 |  | C374 |  | Peptidyl-Prolyl cis-trans isomerase |
| msaCID | I* |  | 5 |  |  |  |  |
|  | J* |  | 6 |  |  |  |  |
|  |  | K* |  | 5 |  |  |  |
|  |  | B |  | 5 |  | C2784 | Serine/threonine-protein kinase |

TABLE 1-continued

QTL associated with the mRNA expression of cold-regulated genes and freezing tolerance in diploid alfalfa. Linkage groups associated with gene expression in leaves or crowns or to freezing tolerance ($LT_{50}$) along with LOD scores are presented. Regulatory genes that map to these genomic regions are identified. The highlighted genes C4494 and C2186 show homology to the CBF1-gene from *Arabidopsis* and the SCOF-1 gene from soybean, respectively, for which an involvement in cold tolerance has been demonstrated.

| | Linkage group | | LOD | | Candidate regulatory gene | | |
|---|---|---|---|---|---|---|---|
| Gene/trait | Crown | Leaf | Crown | Leaf | Crown | Leaf | Homology to genes coding for |
| | E | E | 14 | 8 | msaCID | msaCID | |
| | E | E | 10 | 5 | C5237 | C5237 | Cell division cycle protein 48 |
| | E | E | 12 | 8 | C3346 | C3346 | Ethylene responsive element transcription factor |
| msaCIE | E | E | 7 | 4 | C3283 | C3283 | Ethanolamine kinase |
| | J* | | 5 | | | | |
| | L* | | 6 | | | | |
| | | B | | 8 | | C2784 | Serine/threonine-protein kinase |
| | H* | | 5 | | | | |
| msaCIF | | I* | | 3 | | | |
| msaCIG | | B | | 4 | | C2784 | Serine/threonine-protein kinase |
| | F | | 6 | | msaCIG | | |
| LT50 | C | | 6 | | C2456 | | GTP-binding nuclear protein (RAN1A) |
| | C | | 4 | | C2186 | | Zinc finger transcription factor (SCOF-1 homolog) |
| | E | | 4 | | C5237 | | Cell division cycle protein 48 |
| | E | | 4 | | C3283 | | Ethanolamine kinase |

(*data not shown in FIG. 2).

Example 2

Isolating Regulatory Genes and Regulatory Sequences Associated with QTLs of Interest General Description of the Experimental Approach The detection of QTLs that explain a significant proportion of the variation of the expression of msaCI genes indicates possible localization of regulatory genes at these loci. A number of expressed sequence tags (EST) from cold-acclimated alfalfa encoding genes with know functions in the regulation of gene expression are mapped. Candidate regulatory genes that are located within a QTL associated with the expression of msaCI genes are isolated and characterized, and their expression examined within transgenic alfalfa in order to assess their effect on cold-regulated gene expression.

Description of Candidate Regulatory Genes

A series of ESTs showing homology to genes with known regulatory functions are isolated from a λgt10 cDNA library prepared from mRNA-isolated from crowns of tetraploid alfalfa (*M. sativa* L. cv. Apica; R. Michaud, C. Richard, C. Willemot and H. Gasser 1983. Can. J. Plant Sci. 63: 547-549):

Transcription factors (zinc-finger and AP2 proteins)
Mitogen-activated protein kinases (MMK4, MMK3, MMK2, MMK1)
Calcium-dependent protein kinases
Serine-threonine protein kinase
$Ca^{2+}$ transporting ATPase
GTP binding proteins
RNA binding proteins
Protein phosphatases (type 2A and 2C)
Calmodulin
14-3-3 proteins
GTPase activating proteins
Adenylyl cyclase protein
Phospholipase C
Lipoxygenase
$Ca^{2+}$-binding proteins
Histone deacetylase
Receptor kinase
Phosphatidyl inositol3-kinase Genetic Mapping of Candidate Regulatory Genes Probes for specific regulatory genes listed in table 2 are prepared by PCR amplification, purified on Sephacryl S-200 MicroSpin Columns (Amersham Pharmacia Biotech, Oakville, ON) and stored at −20° C. These probes are used for Southern hybridization to restricted DNA from $F_2$ diploid genotypes of the progeny of the cross described in Example 1. Purified probes are radiolabeled to high specific activity by random hexamer labelling and hybridized to DNA blots according to standard protocols for RFLPs as described in Example 1 (Sambrook, L, Maniatis, T. and Fritsch, 1989. Molecular cloning; A laboratory manual. Cold Spring Harbor Laboratory Press, Cold Spring Harbor, N.Y.). Regulatory genes that are polymorphic and that are being mapped along with their putative functions based on homologies with sequences in GENBANK/EMBL data bases are presented in Table 2.

TABLE 2

Polymorphic regulatory gene and their putative functions. Highlighted clones indicate potential candidate genes involved in the regulation of msaCI genes or freezing tolerance ($LT_{50}$).

| Clone | Homology to |
|---|---|
| C102 | Defender against apoptotic death-1 |
| C103 | Pumilio RNA binding protein |
| C113 | Nucleolin |
| C123 | EF-hand calcium binding protein |
| C127 | MADS transcriptional factor |
| C157 | ABA-induced protein |
| B166 | GTP binding protein |
| A168 | Transcription factor |
| C183 | GTP binding protein |
| B187 | G-box binding protein |
| A207 | Protein kinase C (substrate) |
| C221 | Tyrosine phosphatase |
| A271 | Serine protein kinase |
| C343 | Homeobox protein (knotted-1) |
| C374 | Peptidyl-Prolyl cis-trans isomerase |
| C389 | ABA response enhancer |
| C532 | Helix-loop-helix transcription factor |
| C571 | GTP binding protein |
| C834 | P72 DEAD box protein |
| C948 | Casein kinase |
| C973 | Mitogen activated protein kinase (MMK4) |
| C2105 | WRKY3 DNA binding protein |
| C2186 | Zinc finger transcription factor (SCOF-1 homolog) |
| C2250 | GTP binding protein (Ras-related) |
| C2314 | Phosphatase 2C |
| C2352 | Progesterone binding homolog |
| C2420 | $C^{2+}$ transporting ATPase-like protein |
| C2426 | Ethylene responsive small GTP binding protein |
| C2456 | GTP binding protein (RAN1A) |
| C2595 | Calreticulin |
| C2658 | Calmodulin domain protein kinase (CDPK) |
| C2784 | Serine/threonine protein kinase |
| C2886 | Cyclase-associated protein (CAP) |
| C2939 | AP2 domain transcription factor (TINY-like) |
| C2988 | Leucine rich repeat (LRR) receptor-like protein kinase |
| C3050 | Protein kinase |
| C3125 | Nucleic acid binding protein |
| C3253 | Receptor kinase |
| C3268 | Serine-threonine protein kinase |
| C3283 | Ethanolamine kinase |
| C3291 | IAA-induced ARG-2 protein |
| C3346 | Ethylene responsive transcription factor |
| C3358 | Adenosine kinase |
| C3367 | RNA binding protein |
| C3506 | Protein kinase |
| C3520 | Nucleotide binding protein |
| C3601 | Ring-H2 finger protein |
| C3604 | Transcription factor |
| C3626 | DNA binding protein |
| C3749 | CDC2+/CDC28-related protein kinase R2 |
| C3843 | Phosphatidyl inositol 3-kinase |
| C3844 | GTP binding protein (RAB-type) |
| C4050 | Serine/threonine phosphatase type 2A |
| C4266 | RAC-like protein (RHO homolog) |
| C4320 | Mitogen activatd protein kinase |
| C4438 | 14-3-3 protein |
| C4494 | AP2 domain transcription factor (CBF1 homolog) |
| C4546 | Mitogen activated protein kinase (MAP3K) |
| C4622 | Calmodulin domain protein kinase (CDPK) |
| C5047 | Leucine rich repeat (LRR) receptor-like protein kinase |
| C5206 | Homeobox protein (Knotted-1) |
| C5237 | Cell division cycle protein 48 |

EST sequences are also used to design primers for the amplification of the identified loci as STS (Sequence Tagged Sites) from DNA of the individuals of the segregating population. When the resulting PCR products are monomorphic among the individuals of the population, the PCR products are restricted with various enzymes to detect polymorphism. If no polymorphism is detected the PCR products obtained from the two parents are individually sequenced and SNPs (Single Nucleotide Polymorphims) are searched.

The candidate regulatory genes described above are mapped as RFLPs within the $F_2$ progeny as described in Example 1 in order to assess whether they are localized within QTLs associated with variation in cold-induced expression of msaCI genes as identified in Example 1.

All genes listed in Table 1 and highlighted in table 2 are located in genomic regions containing QTLs and are therefore putative candidate regulatory genes for the expression of msaCI genes, the $LT_{50}$ trait, or a combination thereof. Two of these genes C4494 and C2186 show homology to the CBF1 gene from *Arabidopsis* and the SCOF-1 gene from soybean, respectively, for which an involvement in cold tolerance has been demonstrated (Jaglo-Ottosen, K. R., Gilmour, S. J., Zarka, D. G., Schabenberger, O., and Thomashow, M. F. 1998. *Arabidopsis* CBF1 overexpression induces COR genes and enhances freezing tolerance. Science 280: 104-106. Kim, J. C., Lee, S. H., Chsong, Y. H., Yoo, C-M., Lee, S. L., Chun, H. J., Yun, D. J., Hong, J. C., Lee, S. Y., Lim, C. O., and Cho, M. J., 2001. A novel cold-inducible zinc finger protein from soybean, SCOF-1, enhances cold tolerance in transgenic plants. The Plant Journal 25: 247-259). C4494 (CBF1 homolog) is located at a QTL associated with the expression of msaCIB in leaves (linkage group F, FIG. 2), whereas C2186 (SCOF-1 homolog) is mapping to a region containing a QTL for $LT_{50}$ (linkage group C, FIG. 2). These genes encode cold induced transcription factors that were unequivocally shown to drive the constitutive expression of COR (msaCI) genes in transgenic plants and to increase freezing tolerance under non-acclimated conditions.

The results also indicate a number of interesting novel candidate regulatory genes involved in the expression of cold tolerance and msaCI gene expression (Table 1, FIG. 2). For example the clone C2784, which shows homology to a serine/threonine protein kinase, maps to a location on linkage group B where QTLs for the expression of msaCIA, msaCID, msaCIE and msaCIG in leaves are found. In alfalfa cells, osmotic stress led to the rapid activation of two protein kinases. One of these kinases appears to be a homologue of the ASK1 serine/threonine kinase 1 from *Arabidopsis* (Munnik, T. and H. J. G. Meijer. 2001. FEBS Letters 498: 172-178). Confirmation of the roles of such candidate regulatory genes may be obtained using methodologies outlined below.

Sequencing of Genomic Clones of Candidate Regulatory Genes and Candidate Regulatory Sequences ESTs of candidate regulatory genes that map to one or more QTLs associated with variation of the expression of msaCI genes are isolated from a genomic library constructed in EMBL3 phage (Sambrook, J., Maniatis, T. and Fritsch. 1989. Molecular cloning: A laboratory manual. Cold Spring Harbor Laboratory Press, Cold Spring Harbor, N.Y.), using DNA from the two parents identified above. Each candidate regulatory gene is sequenced in its entirety including upstream and downstream regions of the coding region using the dideoxynucleotide chain termination method (Sambrook, J., Maniatis, T. and Fritsch. 1989. Molecular cloning: A laboratory manual. Cold Spring Harbor Laboratory Press, Cold Spring Harbor, N.Y.). Comparisons between allelic forms from each parent is also made to identify mutations responsible for the QTL. Confirmation of the localization of candidate regulatory genes is carried out by mapping upstream or downstream regions of each regulatory gene on the linkage map generated above. Only regulatory genes that are characterized by having 5' or 3' regions co-mapping with the same one or more QTLs are used for further characterization in complementation or gene knockout studies.

Altered Expression of Candidate Genes in Transgenic Plants (Complementation and Knockout Studies)

Alfalfa transformation is performed using *Agrobacterium tumefaciens* as previously described by Desgagnés et al. (Desgagnés R., S. Laberge, Allard, H. Khoudi, Y. Castonguay, J. Lapointe, R. Michaud and L.-P. Vézina. 1994. Plant Cell Tissue Organ Cult 42: 129-140). Two approaches are taken; 1) Constitutive expression of the candidate gene using a gene fusion to a constitutive promoter, for example, hut not to be limited 35S; and inducible expression. The coding region of the candidate gene is fused in frame to a full-length 35S promoter and the resulting construct is cloned into the binary expression vector pGA482. Full length candidate regulatory genes (i.e. candidate regulatory genes that, with surrounding 5' and 3' regions, map to one or more QTLs identified above) along with approximately 1 kb of 5' and 1 kb of 3' non-coding regions, are cloned into the binary expression vector pGA482. Constructs for both constitutive and inducible expression in the sense orientation are used to transform plants that lacks the allele at the QTL corresponding to expression of the trait of interest (for example, but not to be limited to msaCI gene expression), and the antisense orientation constructs are used to transform plants mat harbor the allele at the QTL. The transgenics are then grown and subject to cold acclimation conditions, as needed to determine the effect of the introduced sense or antisense gene on both expression of one or more msaCI genes and the $LT_{50}$, thereby validating the candidate gene as the regulatory factor controlling mRNA expression of the msaCI genes at the QTL.

All citations are herein incorporated by reference.

The present invention has been described with regard to preferred embodiments. However, it will be obvious to persons skilled in the art that a number of variations and modifications can be made without departing from the scope of the invention as described herein.

The embodiments of the invention in which an exclusive property of privilege is claimed are defined as follows:

1. A method for identifying one or more regulatory sequences mediating expression of one or more genes of interest in an organism comprising:
   i) identifying a first organism of interest characterized in that said first organism of interest exhibits a measurable response to an environmental stimulus;
   ii) identifying a second organism of interest characterized in that said second organism of interest:
      lacks or does not exhibit as strong said measurable response to said environmental stimulus when compared with said first organism of interest;
   iii) crossing said first and second organisms of interest to produce a population of progeny segregating in their response to said environmental stimulus;
   iv) extracting RNA from each individual of said population of progeny and quantifying a level of gene expression of said one or more genes of interest, said one or more genes of interest associated with said response to said environmental stimulus;
   v) identifying one or more Quantitative Trait Locus (QTL), wherein gene expression level is a quantitative trait, and using a marker, or set of markers, that comprise said one or more regulatory sequences, said one or more regulatory sequences mediate said expression of said one or more genes of interest, said one or more genes of interest induced by said environmental stimulus; and
   vi) identifying said one or more regulatory sequences located at said one or more QTL.

2. The method of claim 1, wherein after said step of crossing (step iii)), and prior to said step of extracting RNA (step iv)), said population of progeny are subjected to a desired environmental stimulus or are characterized as being at a specific developmental stage.

3. The method of claim 1, wherein said method is used for identification of said one or more QTL corresponding to a transcription factor or any factor controlling expression of said one or more genes of interest.

4. The method of claim 1, wherein after said step of identifying one or more QTL (step v)), said one or more regulatory sequences located at said one or more QTL are isolated and characterized.

5. The method of claim 1, wherein in said steps of identifying (steps i) and ii)), said environmental stimulus is selected from the group consisting of:
   a biotic stress;
   an abiotic stress;
   an alteration in mineral nutrition;
   an alteration in light quality or flux;
   a response arising from an addition of one or more exogenous chemicals;
   a stress leading to an alteration in levels of endogenous chemicals within a plant;
   a developmental, chemical or environmental control of gene expression during embryogenesis;
   organogenesis;
   senescence;
   maturation;
   dormancy;
   germination;
   circadian, ultradian and other internal rhythms;
   harvestable yield;
   seed set;
   photosynthate translocation;
   an alteration in sink and source capacities within said plant;
   an alteration of leaf area index;
   an alteration of root shoot ratio;
   an alteration in nutritive value of harvested material;
   an alteration in plant morphology;
   a change in rate of cell cycle;
   an alteration in rate of cell differentiation;
   an alteration in cell size;
   an alteration in plant life cycle, and
   genomic rearrangements.

6. The method of claim 1, wherein in said step of identifying (step v), said marker, or said set of markers is identified at said one or more QTL.

7. The method of claim 4, wherein said step of identifying (step vi) is followed by:
   vii) confirming said one or more regulatory sequences is involved in said expression of said one or more genes of interest under conditions of step i) resulting from:
      said measurable response to said environmental stimulus.

8. The method of claim 4, wherein in said one or more regulatory sequence is sequenced.

9. The method of claim 7, wherein said step of identifying (step vi) further comprises:
   mapping one or more candidate regulatory sequences;
   identifying said one or more regulatory sequences mapping with said one or more QTL, said one or more regulatory sequences being a subset of said one or more regulatory sequences;
   isolating said one or more regulatory sequences within said one or more QTL resulting in said one or more isolated regulatory sequences; and
   sequencing said one or more isolated regulatory sequences.

10. The method of claim 7, wherein said step of identifying (step vi), further comprises a step of obtaining said one or more regulatory sequences using positional cloning.

11. The method of claim 7, wherein genetic transformation, gene complementation, gene knock-out techniques, or gene overexpression is used in said step of confirming (step vii), to confirm said one or more regulatory sequences are involved in said expression of said one or more genes of interest.

12. The method of one of claim 1, wherein the organism is a plant.

* * * * *